(12) United States Patent
Yang et al.

(10) Patent No.: US 10,567,655 B2
(45) Date of Patent: Feb. 18, 2020

(54) SYSTEM AND METHOD FOR AUTOMATED EXTRACTION OF HIGH RESOLUTION STRUCTURAL DYNAMICS FROM VIDEO

(71) Applicant: Los Alamos National Security, LLC, Los Alamos, NM (US)

(72) Inventors: Yongchao Yang, Los Alamos, NM (US); Garrett Kenyon, Los Alamos, NM (US); Charles Farrar, Los Alamos, NM (US); David Mascarenas, Los Alamos, NM (US)

(73) Assignee: TRIAD NATIONAL SECURITY, LLC, Los Alamos, NM (US)

(*) Notice: Subject to any disclaimer, the term of this patent is extended or adjusted under 35 U.S.C. 154(b) by 169 days.

(21) Appl. No.: 15/708,986

(22) Filed: Sep. 19, 2017

(65) Prior Publication Data

US 2018/0084195 A1 Mar. 22, 2018

Related U.S. Application Data

(60) Provisional application No. 62/396,695, filed on Sep. 19, 2016.

(51) Int. Cl.
*H04N 5/20* (2006.01)
*H04N 5/232* (2006.01)
(Continued)

(52) U.S. Cl.
CPC .......... *H04N 5/23264* (2013.01); *G01H 9/00* (2013.01); *G01N 29/4472* (2013.01);
(Continued)

(58) Field of Classification Search
CPC .............. H04N 5/23264; H04N 5/232; H04N 21/234363; H04N 21/234381; H04N 5/50;
(Continued)

(56) References Cited

U.S. PATENT DOCUMENTS

2015/0195430 A1* 7/2015 Wadhwa ................ H04N 5/144
348/581

OTHER PUBLICATIONS

Simoncelli et al., "The Steerable Pyramid: A Flexible Architecture for Multi-Scale Derivative Computation", 2nd IEEE International Conference on Image Processing, 1995 (Year: 1995).*

(Continued)

*Primary Examiner* — Qian Yang
(74) *Attorney, Agent, or Firm* — Lewis Roca Rothgerber Christie LLP

(57) ABSTRACT

A method for extracting vibrational modes of a structure includes: receiving a plurality of video frames, each of the video frames including a plurality of pixels; decomposing each of the video frames on a plurality of spatial scales in accordance with complex steerable pyramid filters to obtain a filter response for each of the spatial scales; computing a plurality of local phases of the pixels of each frame; removing a temporal mean from each frame to obtain a plurality of factored vibration motion functions; performing principal component analysis on the factored vibration motion functions to obtain principal components; blind source separating the principal components to compute a plurality of modal coordinates; computing frequency and damping ratios in accordance with the modal coordinates; and outputting the computed frequency and damping ratios.

17 Claims, 26 Drawing Sheets
(12 of 26 Drawing Sheet(s) Filed in Color)

(51) Int. Cl.
*H04N 21/2343* (2011.01)
*G01H 9/00* (2006.01)
*G06T 7/262* (2017.01)
*G01N 29/44* (2006.01)
*G01N 29/46* (2006.01)
*H04N 5/50* (2006.01)

(52) U.S. Cl.
CPC .............. *G01N 29/46* (2013.01); *G06T 7/262* (2017.01); *H04N 5/232* (2013.01); *H04N 21/234363* (2013.01); *H04N 21/234381* (2013.01); *G01N 2291/0234* (2013.01); *G06T 2207/10016* (2013.01); *G06T 2207/20016* (2013.01); *G06T 2207/20056* (2013.01); *G06T 2207/30108* (2013.01); *H04N 5/50* (2013.01)

(58) Field of Classification Search
CPC ............... G01N 29/46; G01N 29/4472; G01N 2291/0234; G06T 7/262; G06T 2207/30108; G06T 2207/20056; G06T 2207/20016; G06T 2207/10016; G01H 9/00

See application file for complete search history.

(56) References Cited

OTHER PUBLICATIONS

Stetter et al. "Principal Component Analysis and Blind Separation of Sources for Optical Imaging of Intrinsic Signals", NeuroImage 2000 (Year: 2000).*

Chowdhury et al., "Computation of Rayleigh Damping Coefficients for Large Systems" Electronic Journal of Geotechnical Engineering, 43:6855-6868, Jan. 2003 (Year: 2003).*

* cited by examiner

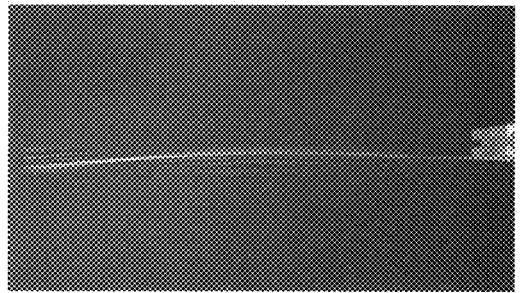
FIG. 20A-4
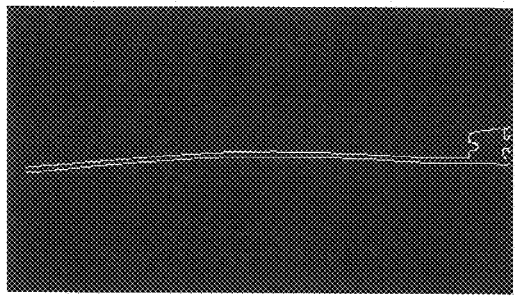
FIG. 20B-4
FIG. 20A-3
FIG. 20B-3
FIG. 20A-2
FIG. 20B-2
FIG. 20A-1
FIG. 20B-1

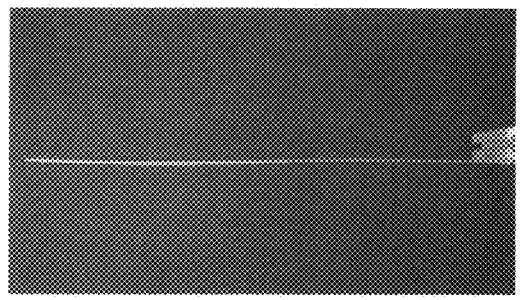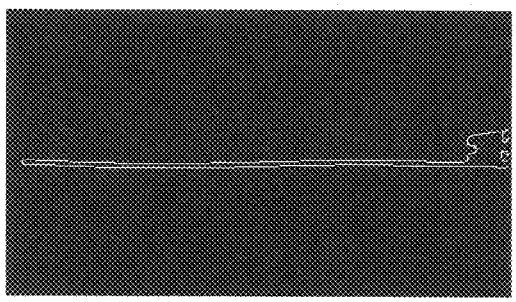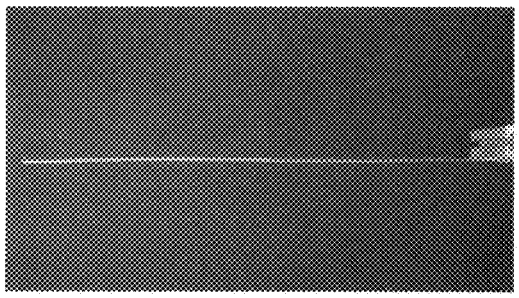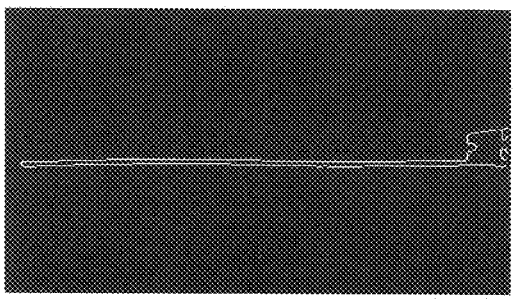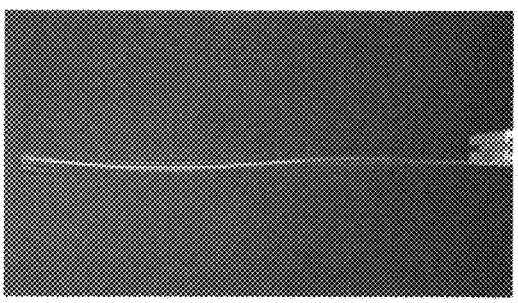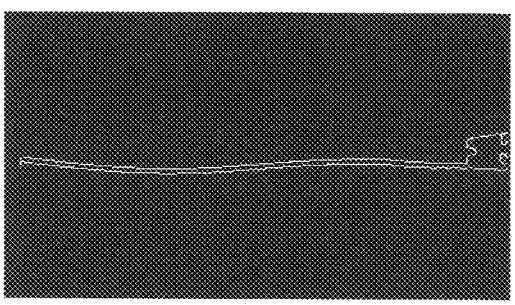

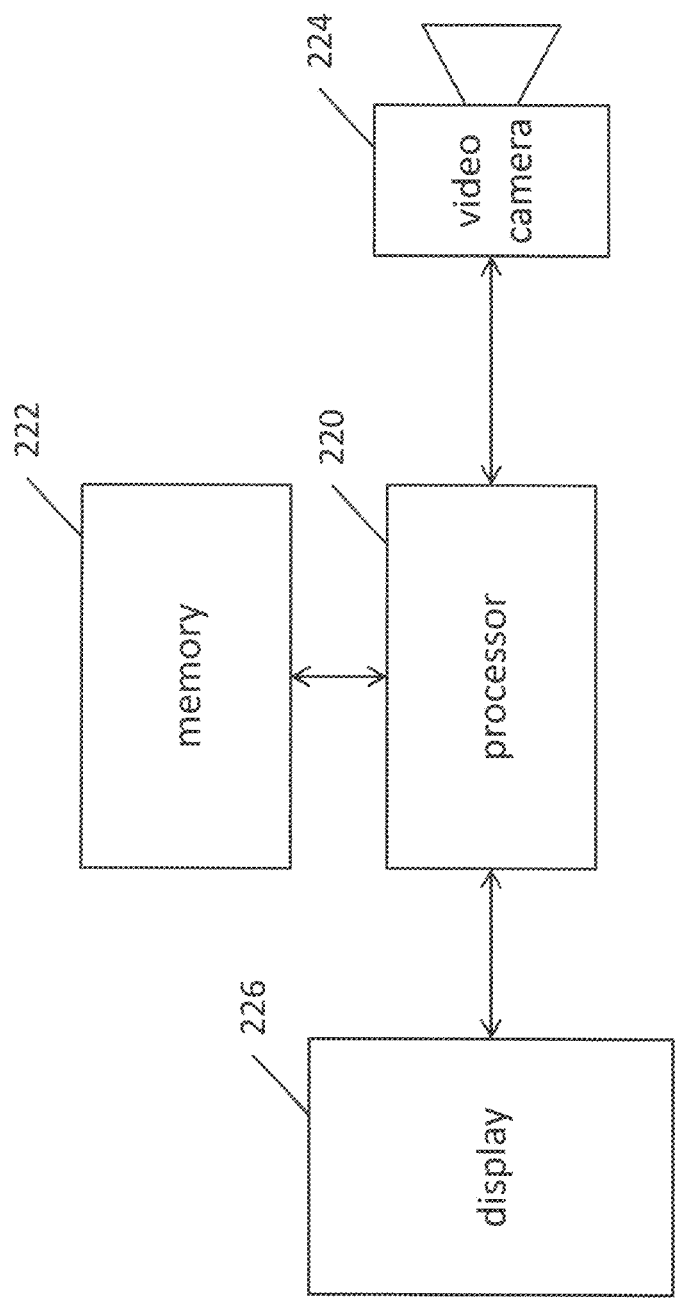

SYSTEM AND METHOD FOR AUTOMATED EXTRACTION OF HIGH RESOLUTION STRUCTURAL DYNAMICS FROM VIDEO

CROSS-REFERENCE TO RELATED APPLICATIONS

This application claims the benefit of U.S. Provisional Patent Application No. 62/396,695 filed in the United States Patent and Trademark Office on Sep. 19, 2016, the entire disclosure of which is incorporated by reference herein.

STATEMENT REGARDING GOVERNMENT RIGHTS

The United States government has rights in this invention pursuant to Contract No. DE-AC52-06NA25396 between the United States Department of Energy and Los Alamos National Security, LLC for the operation of Los Alamos National Laboratory.

FIELD

Aspects of embodiments of the present invention relate to the field of systems and methods for detecting and analyzing vibrational modes in physical structures.

BACKGROUND

Characterizing the dynamics of a physical structure, such as its vibrational modes, is one part of predicting the real-world behavior of the structure. In addition, monitoring these structural dynamics can provide insights into changes to the structure over time, such as the weakening of particular portions of the structure. These characterizations can be used, for example, to evaluate the stability and/or soundness of a structure, in order to ensure that the structure is safe for its users. These physical structures may include, but are not limited to, civil, mechanical, and aerospace structures.

The process of characterizing structural dynamics can be classified as experimental modal analysis or operational modal analysis, where an experimental modal analysis supplies a known input force to the structure, and operational mode analysis relies only on measured response data, without control over the input forces.

Both experimental and operational modal analyses typically require physically-attached wired or wireless sensors such as accelerometers for measuring the vibration of the structures. The sensors themselves can be costly, and installation and maintenance of these sensors can be time-consuming, especially for long-term applications (e.g., structural health monitoring on large civil structures) that require significant maintenance for cabling (e.g., for wired sensors) or periodic replacement of the energy supply (e.g., batteries for wireless sensors). In addition, these physical sensors can result in mass loading on lightweight structures such as aerospace structures, thereby changing the structural dynamics of systems that they are intended to measure. Moreover, these sensors are typically placed at a limited number of discrete locations, and therefore provide low spatial sensing resolution that may be insufficient for modal-based damage localization, or model correlation and updating for larger-scale structures, and may be insufficient for accurately correlating and updating finite element models of the structures.

Non-contact measurement methods such as scanning laser vibrometers can provide high-resolution sensing capacity without the mass-loading effect; however, they make sequential measurements that require considerable acquisition time and can be labor intensive to use when the sensing areas are large. In addition, scanning laser vibrometers are also relatively expensive.

SUMMARY

Aspects of embodiments of the present invention relate to the automatic extraction of vibrational mode data from video data using, for example, computer vision and video processing techniques. Aspects of embodiments of the present invention may enable the characterization of the dynamics of a structure with high spatial resolution and at significantly lower cost than comparative techniques.

According to one embodiment of the present invention, a method for automatically extracting vibrational modes of a structure includes: receiving, by a processor, a plurality of video frames, each of the video frames including a plurality of pixels; decomposing, by the processor, each of the video frames on a plurality of spatial scales in accordance with complex steerable pyramid filters to obtain a filter response for each of the spatial scales; computing, by the processor, a plurality of local phases of the pixels of each frame; removing, by the processor, a temporal mean from each frame to obtain a plurality of factored vibration motion functions; performing, by the processor, principal component analysis on the factored vibration motion functions to obtain principal components; blind source separating, by the processor, the principal components to compute a plurality of modal coordinates; computing, by the processor, frequency and damping ratios in accordance with the modal coordinates; and outputting, by the processor, the computed frequency and damping ratios.

The method may further include magnifying an ith modal coordinate of the modal coordinates by: scaling the ith modal coordinate by a positive coefficient to compute a scaled ith modal component; scaling each non-ith modal coordinate other than the ith modal coordinate by a negative coefficient to compute one or more non-ith scaled modal coordinates; and applying an inverse transform on the scaled ith modal coordinate and the one or more non-ith scaled modal coordinates to compute an ith-mode magnified vibration motion function.

The method may further include outputting the ith-mode magnified vibration motion function as a factored vibration motion function.

The method may further include reconstructing a plurality of ith mode magnified images based on the ith mode magnified vibration motion function. The method may further include outputting the ith magnified images as a video.

The method may further include: performing edge detection on the ith mode magnified image to generate magnified ith mode shapes; and outputting the magnified ith mode shapes. The method may further include outputting the magnified ith mode shapes as a video.

The video frames may be received from a video camera, and the video frames may be captured by the video camera at a rate of at least 240 frames per second.

The video frames may be received from a video camera, and the video frames may be captured by the video camera at a rate of at least 24 frames per second.

According to one embodiment of the present invention, a system for automatically extracting vibrational modes of a structure includes: a processor; and memory coupled to the processor, the memory having instructions stored there on that, when executed by the processor, cause the processor to:

receive a plurality of video frames, each of the video frames including a plurality of pixels; decompose each of the video frames on a plurality of spatial scales in accordance with complex steerable pyramid filters to obtain a filter response for each of the spatial scales; compute a plurality of local phases of the pixels of each frame; remove a temporal mean from each frame to obtain a plurality of factored vibration motion functions; perform principal component analysis on the factored vibration motion functions to obtain principal components; blind source separate the principal components to compute a plurality of modal coordinates; compute frequency and damping ratios in accordance with the modal coordinates; and output the computed frequency and damping ratios.

The memory may further store instructions that, when executed by the processor, cause the processor to magnify an ith modal coordinate of the modal coordinates by: scaling the ith modal coordinate by a positive coefficient to compute a scaled ith modal component; scaling each non-ith modal coordinate other than the ith modal coordinate by a negative coefficient to compute one or more non-ith scaled modal coordinates; and applying an inverse transform on the scaled ith modal coordinate and the one or more non-ith scaled modal coordinates to compute an ith-mode magnified vibration motion function.

The memory may further store instructions that, when executed by the processor, cause the processor to output the ith-mode magnified vibration motion function as a factored vibration motion function.

The memory may further store instructions that, when executed by the processor, cause the processor to reconstruct a plurality of ith mode magnified images based on the ith mode magnified vibration motion function.

The memory may further store instructions that, when executed by the processor, cause the processor to output the ith magnified images as a video.

The memory may further store instructions that, when executed by the processor, cause the processor to: perform edge detection on the ith mode magnified image to generate magnified ith mode shapes; and output the magnified ith mode shapes.

The memory may further store instructions that, when executed by the processor, cause the processor to output the magnified ith mode shapes as a video.

The system may further include a video camera, and the video camera may be configured to capture the video frames at a rate of at least 240 frames per second.

The system of claim 10 may further include a video camera, and the video camera may be configured to capture the video frames at a rate of at least 24 frames per second.

According to one embodiment of the present invention, a system for automatically extracting vibrational modes of a structure includes: means for receiving a plurality of video frames, each of the video frames including a plurality of pixels; means for decomposing each of the video frames on a plurality of spatial scales in accordance with complex steerable pyramid filters to obtain a filter response for each of the spatial scales; means for computing a plurality of local phases of the pixels of each frame; means for removing a temporal mean from each frame to obtain a plurality of factored vibration motion functions; means for performing principal component analysis on the factored vibration motion functions to obtain principal components; means for blind source separating the principal components to compute a plurality of modal coordinates; means for computing frequency and damping ratios in accordance with the modal coordinates; and means for outputting the computed frequency and damping ratios.

The system may further include means for magnifying an ith modal coordinate of the modal coordinates by: scaling the ith modal coordinate by a positive coefficient to compute a scaled ith modal component; scaling each non-ith modal coordinate other than the ith modal coordinate by a negative coefficient to compute one or more non-ith scaled modal coordinates; and applying an inverse transform on the scaled ith modal coordinate and the one or more non-ith scaled modal coordinates to compute an ith-mode magnified vibration motion function.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, together with the specification, illustrate exemplary embodiments of the present invention, and, together with the description, serve to explain the principles of the present invention.

FIGS. 8A-1, 8A-2, 8A-3, and 8A-4 depict a few selected frames from the video captured of an experimental setup shown in FIG. 7A according to one embodiment of the present invention.

FIGS. 8B-1, 8B-2, 8B-3, and 8B-4 depict a few selected frames from the video captured of an experimental setup shown in FIG. 7B according to one embodiment of the present invention.

FIGS. 12A-1, 12A-2, 12A-3, and 12A-4 illustrate a few temporal frames from the motion magnified video (Mode 1, α=8) of the building structure of FIG. 7A, and FIGS. 12B-1, 12B-2, 12B-3, and 12B-4 depict the corresponding mode shapes found by performing edge detection on the frames shown in FIGS. 12A-1, 12A-2, 12A-3, and 12A-4.

FIGS. 13A-1, 13A-2, 13A-3, and 13A-4 illustrate a few temporal frames from the motion magnified video (Mode 2, α=40) of the building structure of FIG. 7A, and FIGS. 13B-1, 13B-2, 13B-3, and 13B-4 depict the corresponding mode shapes found by performing edge detection on the frames shown in FIGS. 13A-1, 13A-2, 13A-3, and 13A-4.

FIGS. 14A-1, 14A-2, 14A-3, and 14A-4 illustrate a few temporal frames from the motion magnified video (Mode 3, α=70) of the building structure of FIG. 7A, and FIGS. 14B-1, 14B-2, 14B-3, and 14B-4 depict the corresponding mode shapes found by performing edge detection on the frames shown in FIGS. 14A-1, 14A-2, 14A-3, and 14A-4.

FIGS. 17A-1, 17A-2, 17A-3, and 17A-4 illustrate a few temporal frames from the non-magnified Video (Mode 3, α=1) of the building structure of FIG. 7A and, FIGS. 17B-1, 17B-2, 17B-3, and 17B-4 depict the corresponding mode shapes found by performing edge detection on the frames shown in FIGS. 17A-1, 17A-2, 17A-3, and 17A-4.

FIGS. 19A-1, 19A-2, 19A-3, and 19A-4 illustrate a few temporal frames from the motion magnified video of the beam structure of FIG. 7B (Mode 1, α=8), and FIGS. 19B-1, 19B-2, 19B-3, and 19B-4 depict the corresponding mode shapes found by performing edge detection on the frames shown in FIGS. 19A-1, 19A-2, 19A-3, and 19A-4.

FIGS. 20A-1, 20A-2, 20A-3, and 20A-4 illustrate a few temporal frames from the motion magnified video of the beam structure of FIG. 7B (Mode 2, α=25) and FIGS. 20B-1, 20B-2, 20B-3, and 20B-4 depict the corresponding mode shapes found by performing edge detection on the frames shown in FIGS. 20A-1, 20A-2, 20A-3, and 20A-4.

FIGS. 21A-1, 21A-2, 21A-3, and 21A-4 illustrate a few temporal frames from the motion magnified video of the beam structure of FIG. 7B (Mode 3, α=45) and FIGS. 21B-1, 21B-2, 21B-3, and 21B-4 depict the corresponding mode shapes found by performing edge detection on the frames shown in FIGS. 21A-1, 21A-2, 21A-3, and 21A-4.

FIG. 22 is a block diagram of a system for automatically extracting vibrational modes of a structure according to one embodiment of the present invention.

DETAILED DESCRIPTION

Figure 1:
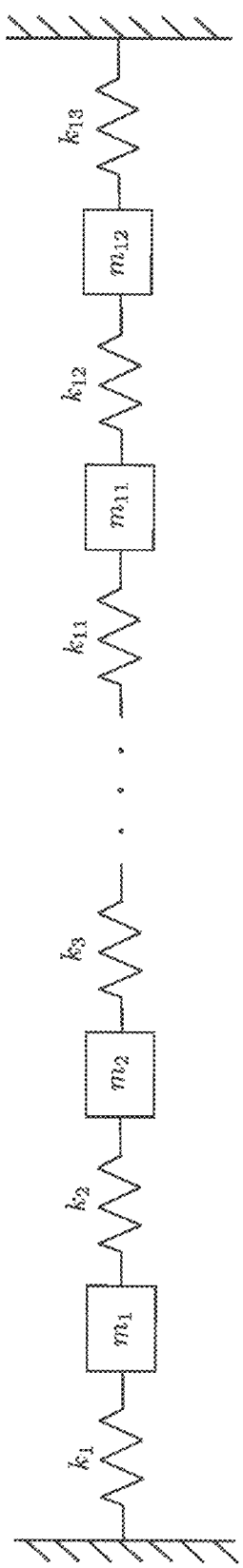
FIG. 1 illustrates a mass-spring-damper system having 12 degrees of freedom that was used in a simulation.

In the following detailed description, only certain exemplary embodiments of the present invention are shown and described, by way of illustration. As those skilled in the art would recognize, the invention may be embodied in many different forms and should not be construed as being limited to the embodiments set forth herein. Like reference numerals designate like elements throughout the specification.

As a non-contact method, digital video cameras are relatively low-cost, agile, and provide high spatial resolution, simultaneous, measurements. Combined with vision based algorithms (e.g., image correlation, optical flow), video camera based measurements have been successfully used for vibration measurements and subsequent modal analysis, based on techniques such as the digital image correlation (DIC) and the point-tracking. However, comparative digital video camera techniques generally require speckle pattern or high-contrast markers to be placed on the surface of structures, which poses challenges when the measurement area is large or inaccessible.

In addition, some related work describe a video processing based method using phase-based optical flow computation and video motion magnification technique for operational modal analysis, without the use of paints or markers on the structure's surface, which also allows the visualization of the vibration modes. However, the procedures of the related work depends on several user input parameters and human supervision that are not suited for efficient and automatic implementation in operational modal analysis. Furthermore, this video motion magnification based technique is unable to handle closely-spaced modes and the related work does not make it clear how to interpret the motion magnification technique in identifying the modal parameters of the analyzed structure.

Some aspects of embodiments of the present invention are directed to the use of video camera systems to capture modal information, even without the use of speckle patterns and/or high contrast markers, and to extract the modal information automatically out of the captured video data. In more detail, by modifying the phase-based video motion magnification framework, aspects of embodiments of the present invention provide an output-only (video measurements) modal analysis algorithm that requires no structural surface preparation (e.g., in the form of speckle patterns or high contrast markers) and that can be implemented in a relatively efficient and autonomous manner. Some aspects of embodiments of the present invention use a multiscale pyramid decomposition and representation method and an unsupervised learning approach (blind source separation or BSS) to extract, model, and manipulate the full-field spatiotemporal pixel phases that encode the local structural vibration using only the video measurements.

Systems and methods according to embodiments of the present invention are able to blindly and accurately extract resonant frequencies, damping ratios, and high-resolution mode shapes of the structure captured in the video. Embodiments of the present invention require little user input and/or supervision to blindly identify modes using BSS, which is able to handle closely-spaced modes.

Furthermore, as noted above, aspects of embodiments of the present invention utilize the video measurements to perform modal analysis of structures without additional structural surface preparation. This characteristic reduces the cost of performing such analyses (e.g., the cost of installing sensors and/or high contrast markers or the costs of using a projected speckle pattern, as well as the cost of having a trained operator manually adjust input parameters and supervise the process of extracting vibrational data using the related work technique), thereby allowing the use of modal analysis in circumstances where the costs may otherwise have been prohibitively high.

According to one embodiment, a multi-scale image processing method is applied on the frames of the video of a vibrating structure to extract the local pixel phases that encode local structural vibration, establishing a full-field spatiotemporal motion matrix. A high-spatial dimensional, yet low-modal-dimensional, over-complete model is used to represent the extracted full-field motion matrix using modal superposition, which is physically connected and manipulated by a family of unsupervised learning models and techniques, respectively. Thus, embodiments of the present invention are able to blindly and accurately extract modal frequencies, damping ratios, and full-field (as many points as the pixel number of the video frame) mode shapes of the structure. As discussed in more detail below, the method is validated by laboratory experiments on a bench-scale building structure and a cantilever beam. As such, aspects of embodiments of the present invention are directed to systems and methods for generating output (video measurements)-only identification and visualization of the weakly-excited modes.

In addition, aspects of embodiments of the present invention relate to applying motion magnification to make it easier for a system or method according to embodiments of the present invention to identify the weakly excited modes that may have subtle vibration motion, and to make it easier which is quite common and challenging in operational modal identification, especially in the presence of noise.

Mathematical Analysis

Structural vibration can be measured in video recordings containing frames with temporally displaced or translated image intensity $I(x+\delta(x,t))$ where x is the pixel coordinate (e.g., x is a two-dimensional coordinate) and $\delta(x,t)$ is the spatially local, temporally varying motion (e.g., varying from frame-to-frame). For the sake of convenience, these image frames I will be described in the context of video data captured by digital video cameras. However, embodiments of the present invention are not limited thereto.

Among the widely-used image processing techniques for motion estimation, basically, digital image correlation and other similar template matching methods estimate $\delta(x,t)$ by maximizing the image intensity correlation between a current frame $I(x+\delta(x,t))$ and a reference frame $I(x)$, while optical flow techniques estimate the motion field by regularizing the current and reference frames under the optical flow or image brightness consistency constraint.

Both template matching methods and optical flow techniques are based on image intensity. Just as oscillating motion can be characterized by its magnitude and phase using Fourier transform, structural vibration motion is encoded in the local amplitudes and local phases of the image measurements, which can be extracted by applying multi-scale, localized filters. In particular, phase information has been shown to provide a better approximation of the motion than amplitudes (related to the intensity strength) and phase information is relatively insensitive to changes in illumination, perspective, and surface conditions, making it more suitable in many real-world applications over the original image intensity information.

Aspects of embodiments of the present invention relate to a phase-based output-only (video measurement) modal identification method that can extract modal frequencies, damping ratios, and high-resolution mode shapes of structures. This method is robust to noise, as will be discussed in more detail below.

Local Phase-Based Vibration Motion Representation

Because $\delta(x,t)$ encoded in $I(x+\delta(x,t))$ is spatially local, transforms (filters) that are spatially multi-scale and localized are used to extract the local phases. One such transform is the wavelet transform; however, its sub-band representation is aliased, and therefore generally is not suited for motion representation and estimation.

On the other hand, the complex steerable pyramid has multi-scale, localized, non-aliasing sub-bands and can be used to extract the local amplitudes and local phases. As such, one embodiment of the present invention applies complex steerable pyramid filters (e.g., complex Gabor filters that are sinusoids (with spatial frequency $\omega_0$) windowed by a Gaussian envelop leading to finite spatial support) to each frame (N pixels) of the video (T time samples) to build a pyramid. Collapsing this constructed pyramid yields Equation (1):

$$I(x+\delta(x,t)) = \sum_{\omega=-\infty}^{\infty} R_\omega(x,t) = \sum_{\omega=-\infty}^{\infty} \rho_\omega(x,t)e^{j2\pi\omega_0(x+\delta(x,t))}$$

where $R_\omega(x,t)$ is the subband representation (filter response) on the spatial scale $\omega$ as defined by Equation (2):

$$R_\omega(x,t)=\rho_\omega(x,t)e^{j2\pi\omega_0(x+\delta(x,t))}$$

with local amplitude $\rho_\omega(x,t)$ (corresponding to edge strength) and the local phase:

$$\psi(x,t)=2\pi\omega_0(x+\delta(x,t))=2\pi\omega_0 x+2\pi\omega_0\delta(x,t)$$

that encodes the temporal vibration motion of the structure.

Modal Expansion of the Phase-Based Vibration Motion

After applying the complex steerable pyramids to the frames of the video, on each spatial scale w, the obtained local phase $\psi(x,t)$ contains the vibration motion $\delta(x,t)$, upon which output-only modal identification can be conducted. Let $\delta'(x,t)=2\pi\omega_0\delta(x,t)$ after removing the (temporal) mean, $2\pi\omega_0 x$, of the phase $\psi(x,t)$. The ($2\pi\omega_0$-factored) vibration motion $\delta'(x,t)$ can be expressed by the modal expansion as a linear combination of the modal responses as shown in Equation (3):

$$\delta'(x,t) = \Phi(x)q(t) = \sum_{i=1}^{n} \varphi_i(x)q_i(t)$$

where n is the mode number, $\Phi \in \mathbb{R}^{N \times n}$ (on Scale 1 the pixel dimension is N) is the mode shape matrix with $\varphi_i(x)$ as the ith mode shape, and $q \in \mathbb{R}^{n \times T}$ is the modal response vector with $q_i(t)$ as the ith modal coordinate. For output-only modal identification, both of $\Phi$ and $q(t)$ are to be identified from the obtained local phase $\delta'(x,t)$ only. Because the pixel (spatial) dimension of $\delta'(x,t)$, N is much higher than the modal dimension (number), n, i.e., N>>n, Equation (3) is a high-spatial-dimensional, low-modal dimensional over-complete model representing the spatiotemporal $\delta'(x,t)$ and the output-only modal identification problem above cannot be directly solved.

As such, according to some embodiments of the present invention, a family of unsupervised machine learning approaches known as blind source separation (BSS), is used to explicitly model and tackle this over-complete output-only modal identification problem because of their efficient and effective identification capability that requires little user supervision.

In one embodiment of the present invention, the BSS-based method includes dimension reduction and modal separation.

Dimension Reduction by Principal Component Analysis (PCA)

According to one embodiment of the present invention, dimension reduction of the over-complete system described by Equation (3) is accomplished by principal component analysis or PCA. The principal components are closely related to the modal components and PCA has the advantage of preserving the high spatial resolution vibration information.

Starting with the singular value decomposition or SVD of the motion matrix $\delta' \in \mathbb{R}^{N \times T}$ assuming, without loss of generality, that N>T, Equation (4):

$$\delta' = U\Sigma V^* = \sum_{i=1}^{n} \sigma_i u_i v_i^*$$

where $\Sigma \in \mathbb{R}^{N \times T}$ is a diagonal matrix containing T diagonal elements, where $\sigma_i$ is the ith singular value ($\sigma_1 \geq \ldots \geq \sigma_i \geq \ldots \geq \sigma_T \geq 0$), and $U=[u_1, \ldots, u_N] \in \mathbb{R}^{N \times N}$ and $V=[v_1, \ldots, v_T] \in \mathbb{R}^{T \times T}$ are the matrices of the left- and right-singular vectors obtained by the eigenvalue decomposition (EVD) of the covariance matrices of $\delta'$ shown in Equations (5) and (6):

$$\delta'\delta'^* = U\Sigma^2 U^*$$

$$\delta'^*\delta' = V\Sigma^2 V^*$$

The rank of $\delta'$ is r if the number of non-zero singular values is r ($\sigma_1 \geq \ldots \geq \sigma_r \geq \sigma_{r+1} = \ldots = \sigma_T = 0$).

The ith singular value $\sigma_i$ is related to the energy projected onto the ith principal direction (vector) $u_i$ of $\delta'$. In structural dynamic analysis, for an undamped or very lightly damped structure, if its mass matrix is proportional to the identity matrix (uniform mass distribution), then the principal directions will converge to the mode shape direction with the corresponding singular values indicating their participating energy in the structural vibration responses $\delta'$. In other words, the active modes of the structure, under broadband excitation, are projected onto the r principal components.

An empirical, but usually true, observation is that typically there are only few dominant active modes present in the structural vibration responses, so the rank of $\delta'$, r, which is approximately the number of active singular values ($\sigma_1 \geq \ldots \geq \sigma_r \geq \sigma_{r+1} \approx \ldots \approx \sigma_T \approx 0$), is very small compared to the spatial dimension of $\delta$, N. In other words, r<<N. Therefore PCA is able to conduct significant dimension reduction on $\delta'$ by linearly projecting most energy (modal components) of $\delta'$ onto a small number of principal components, as represented in Equation (7):

$$\eta = U_r^* \delta'$$

where $U=[u_1, \ldots, u_r] \in \mathbb{R}^{N \times r}$ is the first r (<<N) columns of U, and the ith row of the resultant $\eta=[\eta_1, \ldots, \eta_r]^* \in \mathbb{R}^{r \times T}$, $\eta_i$ is the ith principal component of $\delta'$. Note that the above linear, invertible PCA transform preserves the high spatial resolution of the low-rank $\delta' \in \mathbb{R}^{N \times T}$ by its inverse transform (projection) of $\eta \in \mathbb{R}^{r \times T}$ back to, as shown in Equation (8):

$$\delta' = U_r \eta$$

Modal Separation Through the Blind Identification of Vibration Modes

As shown above with respect to Equations (4), (5), (6), and (7), the active mode components within $\delta' \in \mathbb{R}^{N \times T}$ are projected to $\eta \in \mathbb{R}^{r \times T}$ (so r≈n) by principal component analysis (PCA). Because the uniform mass distribution assumption is generally not satisfied, each principal component of $\eta \in \mathbb{R}^{r \times T}$ is still a mixture of modes and can also be expressed as a linear combination of the modal coordinates, as shown in Equation (9):

$$\eta(t) = \Upsilon q(t) = \sum_{i=1}^{r} \gamma_i q_i(t)$$

Substituting Equations (3) and (9) into Equation (8) yields Equation (10):

$$\sum_{i=1}^{n} \varphi_i q_i(t) = \delta' \approx U_r \eta = U_r \Upsilon q(t) = U_r \sum_{i=1}^{r} \gamma_i q_i(t) = \sum_{i=1}^{r} (U_r \gamma_i) q_i(t)$$

Comparing the two ends of Equation (1) with r n, it is approximately true that, as shown in Equation (11):

$$\varphi_i = U_r \gamma_i$$

Research in structural dynamics has established a one-to-one mapping between the modal expansion and the linear mixture model of the BSS techniques, which can perform very efficient output-only modal identification. While a family of BSS techniques is suited for output-only modal identification, some embodiments of the present invention are directed to using the complexity pursuit (CP) algorithm, as it has been shown to be is efficient and able to identify closely-spaced and highly-damped modes with little expert supervision and parameter adjustment. Therefore using CP, $\eta(t)$ can be directly de-coupled or separated into individual modal coordinates, as shown in Equation (12):

$$q(t) = W\eta(t)$$

simultaneously yielding the "de-mixing" or "de-coupled" matrix $W \in \mathbb{R}^{r \times r}$ and the modal coordinates q(t). Comparing Equations (9) and (12), $\gamma \in \mathbb{R}^{r \times r}$ can then be estimated as the inverse of W by Equation (13):

$$\gamma = W^{-1}$$

Therefore, mode shapes $\varphi_i(x)$, with very high spatial resolution (every pixel measurement on the structure), can be estimated in accordance with Equations (11) and (13). Modal frequencies and damping ratios can be estimated from the modal coordinates $q_i(t)$ by, respectively, Fourier transform and logarithm decrement techniques, or by using Hilbert transform (HT) based single-degree-of-freedom (SDOF) analysis.

Numerical Validation of Principal Component Analysis-Complexity-Pursuit (PCA-CP) for Output-Only Modal Identification of Over-Complete System Numerical simulations can be used to validate the above method for output-only modal identification in an over-complete setting. FIG. 1 illustrates a mass-spring-damper system having 12 degrees of freedom that was used in a simulation of an application of a technique according to embodiments of the present invention. The mass-spring damper system was constructed with the following parameters: diagonal mass matrix M with $m_1=2$, $m_2=\ldots=m_{11}=1$, $m_{12}=3$, stiffness $k_1=\ldots k_{13}=20000$, and proportional damping matrix $C=\alpha M$ with $\alpha=3$. Free vibration was simulated by an initial unit velocity at the 12th degree of freedom. 10-second 12-channel structural responses x(t) were computed by the Newmark-beta algorithm with a sampling frequency of 1000 Hz.

An over-complete scenario was simulated as follows. First, twelve theoretical modal coordinates q(t) were obtained by multiplying x(t) by the inverse of the theoretical mode shape matrix $\Phi$; that is, $q(t)=\Phi^{-1} x(t)$. Then, only the first 4 modes were used to reconstruct a new set of structural responses $\bar{x}(t)=\Sigma_{i=1}^{4}\varphi_i q_i(t)$. Therefore, the new $\bar{x}(t)$ contained 12-channel structural responses but only four modes, which is over-complete.

Figure 2:
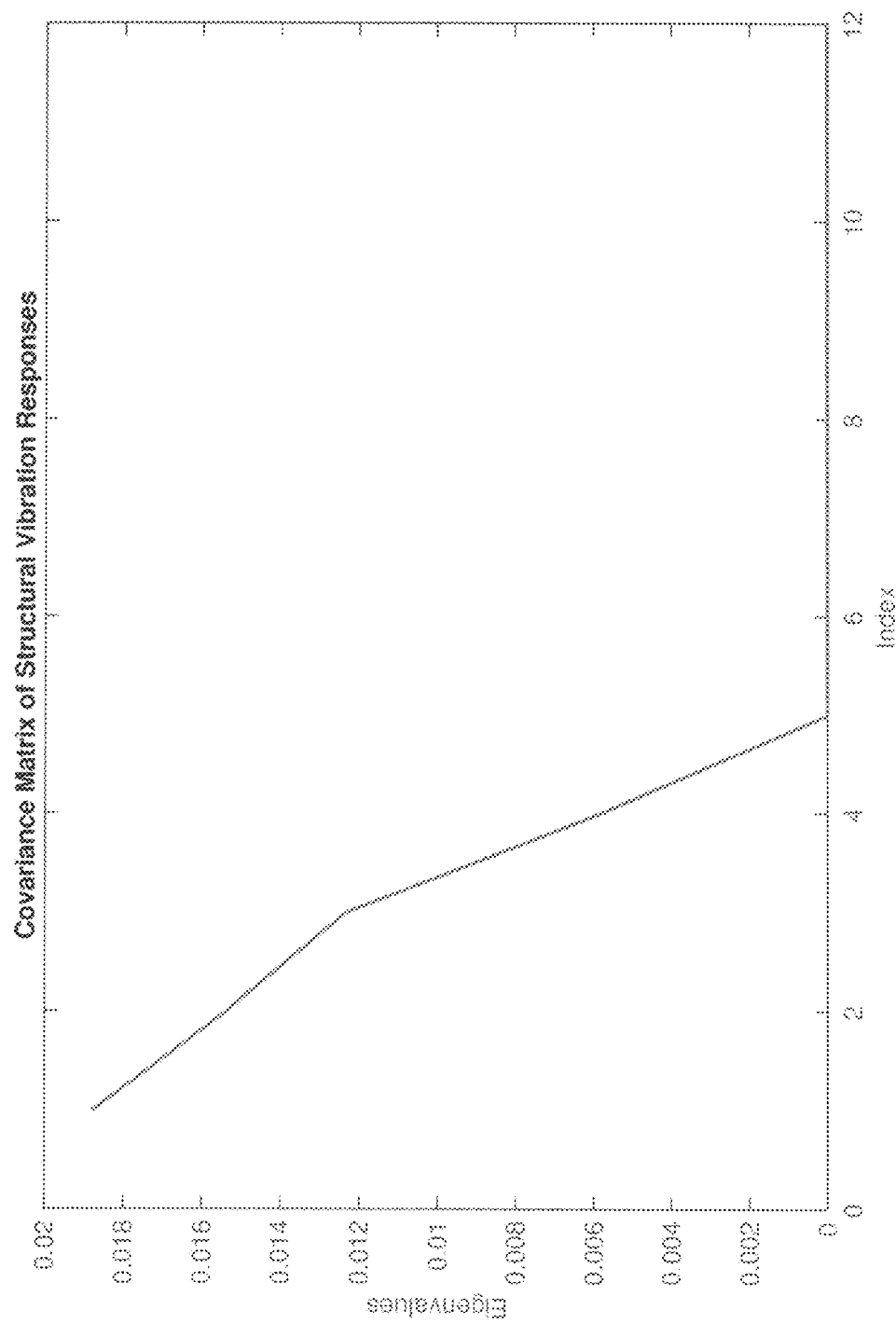
FIG. 2 is a graph showing the eigenvalue distribution of the covariance matrix of the structural responses of the numerical model with over-complete setting.

The Principal Component Analysis-Complexity Pursuit (PCA-CP) algorithm was then applied on $\bar{x}(t)$ as per Equations (4) through (13). FIG. 2 is a graph showing the eigenvalue distribution of the covariance matrix of the structural responses of the numerical model with over-complete setting, and shows that there are only 4 active non-zero eigenvalues (squares of the singular values), indicating most of the modal components contained in the 12-channel $\bar{x}(t)$ have been projected onto the first four principal components, which is depicted in FIG. 3.

Figure 3:
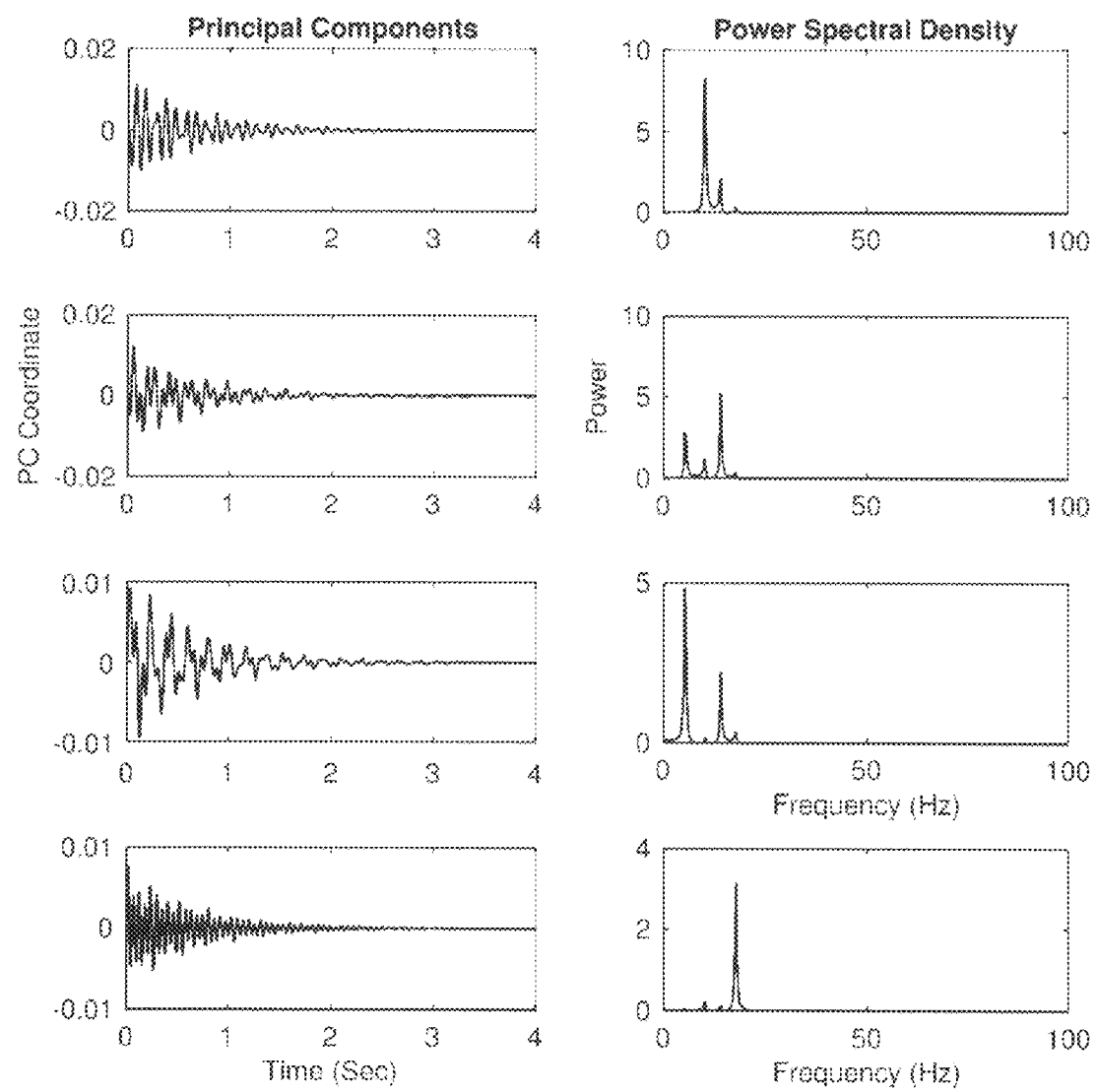
FIG. 3 is a set of graphs that show the principal components and their power spectral density (PSD) of the structural responses of the numerical model.

FIG. 3 is a set of graphs that show the four principal components and their power spectral density (PSD) of the structural responses of the numerical model. FIG. 3 shows that while each of the four principal components contains one dominant mode of the four modes (e.g., in the power spectral density graphs for each of the four principal components, there is one peak that is noticeably taller than the others), respectively, it is still a mixture of the four modes (there are still other peaks is in the power spectral density).

Figure 4:
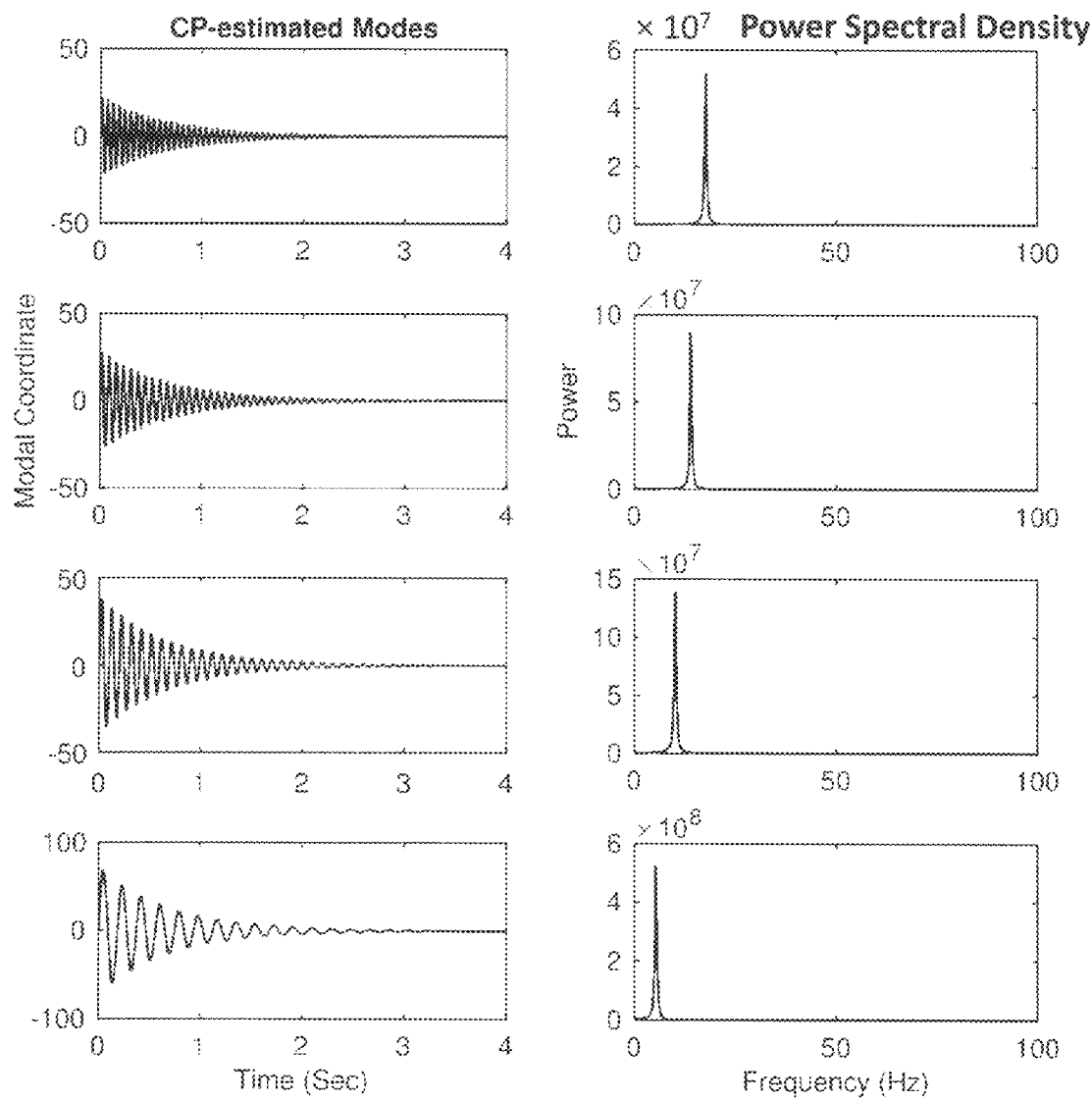
FIG. 4 depicts the estimated modal coordinates by the complexity pursuit (CP) algorithm applied on the active principal components of the structural responses of the numerical model.

FIG. 4 depicts the estimated modal coordinates by the complexity pursuit (CP) algorithm applied on the active principal components of the structural responses of the numerical model. After applying CP on these four principal components according to Equation (12), as shown in FIG. 4, they are completely separated into four individual modal coordinates (e.g., each of the power spectral density graphs has a single peak), upon which Hilbert transform-based Single Degree of Freedom (SDOF) analysis methods are performed to extract the modal frequencies and damping ratios.

Figure 5:
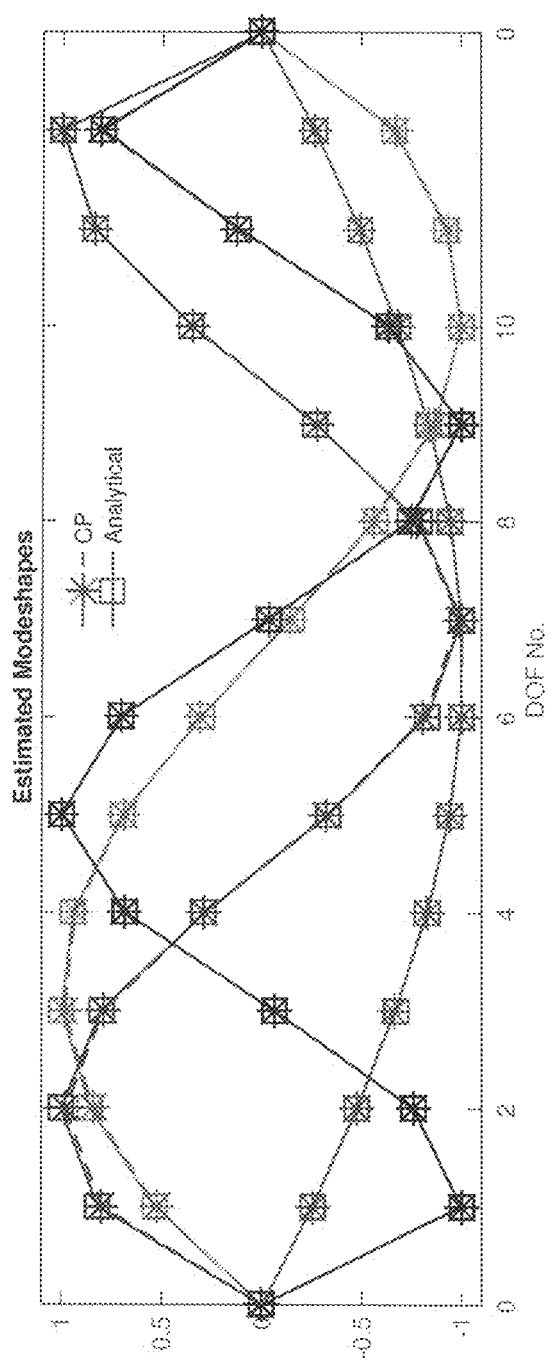
FIG. 5 illustrates the mode shapes estimated by the PCA-CP algorithm compared with the analytical ones of the numerical model.

FIG. 5 illustrates the mode shapes estimated by the PCA-CP algorithm compared with the analytical ones of the numerical model. (Red: Mode 1; Green: Mode 2; Blue: Mode 3; Black: Mode 4; Star markers: Estimated; Square markers: Analytical). The mode shapes were estimated according to Equation (11) and shown in FIG. 5. Table 1, below, lists the estimated modal parameters which are compared with the theoretical ones, indicating they match each other very well, and validating the effectiveness of the PCA-CP algorithm for output-only modal identification of over-complete systems.

TABLE 1

Modal parameters of an over-complete numerical system estimated by PCA-CP

| Mode | Frequency (Hz) | | Damping ratio (%) | | MAC |
|---|---|---|---|---|---|
| | Theoretical | Estimated | Theoretical | Estimated | |
| 1 | 5.3503 | 5.3448 | 4.46 | 4.48 | 1.0000 |
| 2 | 10.1317 | 10.1269 | 2.36 | 2.36 | 0.9999 |
| 3 | 13.9983 | 13.9920 | 1.71 | 1.71 | 0.9999 |
| 4 | 17.6846 | 17.6738 | 1.35 | 1.35 | 1.0000 |

Motion Magnification

As discussed above, aspects of embodiments of the present invention relate to the blind extraction of modal parameters, including frequencies, high-resolution mode shapes, and damping ratios, from supplied video data.

Because methods according to embodiments of the present invention do not make assumptions regarding the number of modes, it is able to identify as many modes as are present in the vibration response measurements (e.g., in the video data). However, in operational or output-only modal identification, some modes, usually higher modes, are very difficult to excite out; as a result, these modes are only weakly or subtly present in the structural vibration responses $\delta'$. While modal frequencies and damping ratios of these weakly-excited modes (e.g., those having very subtle vibration motion) may still be estimated reasonably accurately, the accuracy of these estimated mode shapes is significantly undermined and easily contaminated by noise, even though the mode shapes may be captured at very high resolution (e.g., involving a large number of pixels). This issue can be addressed by further manipulating the modal contents in the video measurements using the phase-based motion magnification technique, which is robust to noise.

Magnification of an Individual Vibrational Mode

After extracting the individual modal coordinates $q_i(t)$, motion magnification or attenuation can then be applied on the isolated modal coordinates. In one embodiment magnifies the ith mode as follows: First, multiply the ith mode $q_i(t)$ by a magnification factor $\alpha$ and multiply the other modes (the "non-ith" modes) $q_k(t)$ $(k\in[1,r]\neq i)$ by an attenuation factor $\beta$ (e.g., $\beta=-1$) and substitute into Equation (9) to yield Equation (14):

$$\hat{\eta}(t) = \Upsilon\hat{q}(t) = \gamma_i(\alpha q_i(t)) + \sum_{k=1,k\neq i}^{r} \gamma_k(\beta q_k(t)) = \alpha\gamma_i q_i(t) + \sum_{k=1,k\neq i}^{r} -\gamma_k q_k(t)$$

where ^("hat") denotes "magnified." Substituting Equation (9) into Equation (14) yields Equation (15):

$$\hat{\eta}(t) = $$
$$\alpha\gamma_i q_i(t) + \sum_{k=1,k\neq i}^{r} -\gamma_k(q_k(t)) = \alpha\gamma_i q_i(t) + \gamma_i q_i(t) - \eta = (1+\alpha)\gamma_i q_i(t) - \eta$$

Further reconstructing $\hat{\mathbb{N}}$ using Equations (8) and (15) yields Equation (16):

$$\hat{\mathbb{N}} \approx U_r\hat{\eta} = U_r[(1+\alpha)\gamma_i q_i(t)-\eta] = (1+\alpha)(U_r\gamma_i)q_i(t)-U_r\eta$$

Now substituting Equations (11) and (8) into Equation (16) yields Equation (17):

$$\hat{\mathbb{N}} \approx (1+\alpha)(U_r\gamma_i)q_i(t)-U_r\eta = (1+\alpha)\varphi_i q_i(t)-\delta'$$

The effect of motion magnification is seen via phase manipulation (e.g., phase shift) by multiplying the original sub-band representation $R_\omega(x,t)$ by $e^{j\delta'}$ and following Equations (2) and (17) yields Equation (18):

$$\hat{R}_\omega(x, t) = R_\omega(x, t)e^{j\delta'} = \rho_\omega(x, t)e^{j(2\pi\omega_0 x+\delta'+\hat{\delta}')} = \rho_\omega(x, t)e^{j\left\{2\pi\omega_0\left[x+\frac{(1+\alpha)\varphi_i q_i(t)}{2\pi\omega_0}\right]\right\}}$$

Compared to the original Equation (2), expanded by Equation (3), denoted as Equation (19):

$$R_\omega(x, t) = \rho_\omega(x, t)e^{j(2\pi\omega_0 x+\delta'(x,t))} = \rho_\omega(x, t)e^{j\left\{2\pi\omega_0\left[x+\frac{\varphi_i(x)q_i(t)}{2\pi\omega_0}+\sum_{k=1,k\neq i}^{n}\frac{\varphi_k(x)q_k(t)}{2\pi\omega_0}\right]\right\}}$$

It can be seen from the right sides of Equations (18) and (19) that the motion of the ith mode has been magnified by $(1+\alpha)$ times and the motion of other modes ($k\neq i$) have been removed. In other words, the ith mode has been blindly separated (by removing other modes in the images/video measurements) and magnified by phase manipulation as per Equations (14) through (19). Performing such phase manipulation procedures on each sub-band scale ω, the reconstructed images (which, when shown in sequence produce a video in which the selected mode is amplified) contain only the magnified vibration motion of the ith mode, whose vibration is readily visualized in $\hat{I}$, as shown in Equation (20):

$$\hat{I}(x+\delta'(x, t)) = \sum_{\omega=-\infty}^{\infty} \hat{R}_\omega(x, t) = \sum_{\omega=-\infty}^{\infty} \rho_\omega(x, t)e^{j\left\{2\pi\omega_0\left[x+\frac{(1+\alpha)\varphi_i q_i(t)}{2\pi\omega_0}\right]\right\}}$$

Afterwards, standard image edge detection can be performed on $\hat{I}$ to segment or separate the structure from the background, thereby obtaining the high-resolution vibration mode shapes of the structure (similarly, the images, when arranged in sequence, form a video in which the selected or ith mode is magnified). Other modes can be blindly separated and magnified along the same procedures as per Equations (14) through (20).

As such, aspects of embodiments of the present invention are also directed to automatically generating modified video data from original video data captured of a structure, where, in the modified video data, one of the vibrational modes of the structure is amplified. Embodiments of the present invention are also directed to automatically extracting the vibration mode shapes of the structure by applying edge detection to the modified video data. Furthermore, multiple videos may be generated—one for each of the vibrational models, as well as one for each of the spatial scales ω.

Signal (Weak Mode Motion) to Noise Ratio Analysis

As per Equations (14) through (20), even the subtle vibration motion of the weakly-excited modes is magnified by $(1+\alpha)$ times in the reconstructed video $\hat{I}$ containing only one individual mode, which is advantageous for the following mode shape estimation by edge detection. The noise robustness of the motion magnification based method is analyzed below.

If the image $I(x+\delta(x,t))$ is contaminated by noise $n(x,t)$, the sub-band representation of the noisy image $I(x+\delta(x,t))+n(x,t)$ can be represented by Equation (21):

$$\tilde{R}(x,t) = \rho_\omega(x,t)e^{j2\pi\omega_0(x+\delta(x,t))} + \mathbb{N}_\omega(x,t)$$

where "~" denotes "noisy" and $\mathbb{N}_\omega(x,t)$ is the sub-band of the noise. Assuming that the amplitude of the noiseless image $\rho_\omega(x,t)$ is much larger than that of $\mathbb{N}_\omega(x,t)$, then the extracted phase of $\tilde{R}_\omega(x,t)$ will still be $\psi(x,t)=2\pi\omega_0(x+\delta(x,t))$ as well, per Equations (3) through (17). Applying the phase magnification to $\tilde{R}_\omega(x,t)$ in accordance with Equation (18) results in Equation (22):

$$\hat{\tilde{R}}_\omega(x, t) = R_\omega(x, t)e^{j\delta'} + \mathbb{N}_\omega(x, t)e^{j\delta'}$$
$$= \rho_\omega(x, t)e^{j\left\{2\pi\omega_0\left[x+\frac{(1+\alpha)\varphi_i q_i(t)}{2\pi\omega_0}\right]\right\}} + \mathbb{N}_\omega(x, t)e^{j[(1+\alpha)\varphi_i q_i(t)-2\pi\omega_0\delta(x,t)]}$$

As seen from Equation (22), while the vibration motion of the ith mode has been magnified by $(1+\alpha)$ times in the noiseless image, the magnification only shifts the phase of the noise component and does not change the noise amplitudes. Therefore, after collapsing the sub-bands, the reconstructed video (or images) $\hat{I}$ with noise is expressed in Equation (23):

$$\hat{I} = \sum_{\omega=-\infty}^{\infty} \hat{R}_\omega(x, t) = \sum_{\omega=-\infty}^{\infty} \rho_\omega(x, t)e^{j\left\{2\pi\omega_0\left[x+\frac{(1+\alpha)\varphi_i q_i(t)}{2\pi\omega_0}\right]\right\}} + \mathbb{N}_\omega(x, t)e^{j[(1+\alpha)\varphi_i q_i(t)-2\pi\omega_0\delta(x,t)]}$$

As seen in Equation (23), the reconstructed images have $(1+\alpha)$ times magnified vibration motion of the ith mode with the same noise intensity level, and therefore the magnification does not have a significant impact on performing edge detection on the reconstructed video (or images) to extract the magnified mode shape of the weakly-excited modes, whose subtle vibrations may be easily buried in noisy images.

Systems and According to Embodiment of the Present Invention

Accordingly, embodiments of the present invention are related to the use of an unsupervised learning technique such as blind source separation and the use of video motion magnification to blindly and automatically extract vibrational mode information using video measurements of a structure.

Figure 6A:
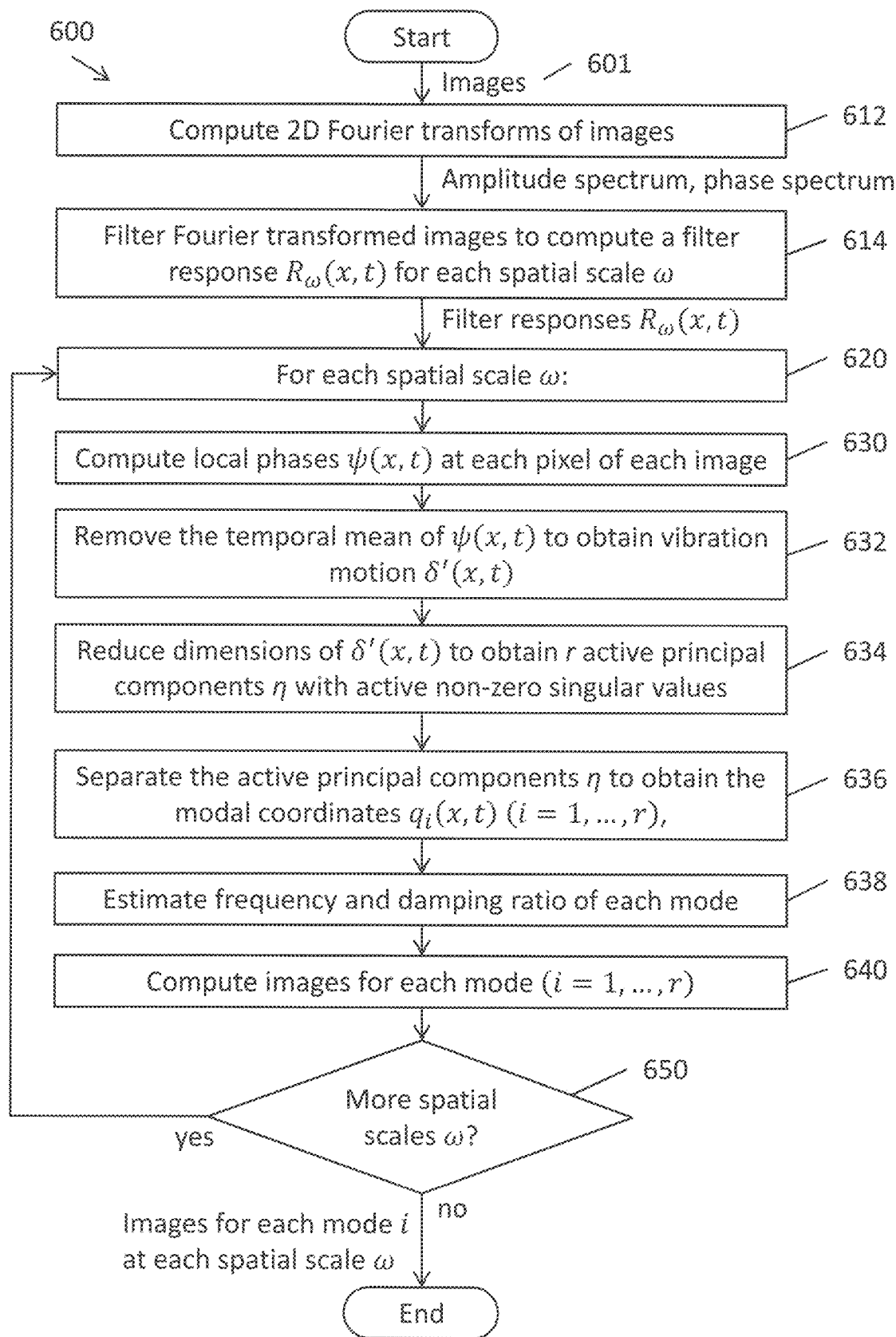
FIGS. 6A, 6B, and 6C are flowcharts illustrating a method of computing according to one embodiment of the present invention.
Figure 6B:
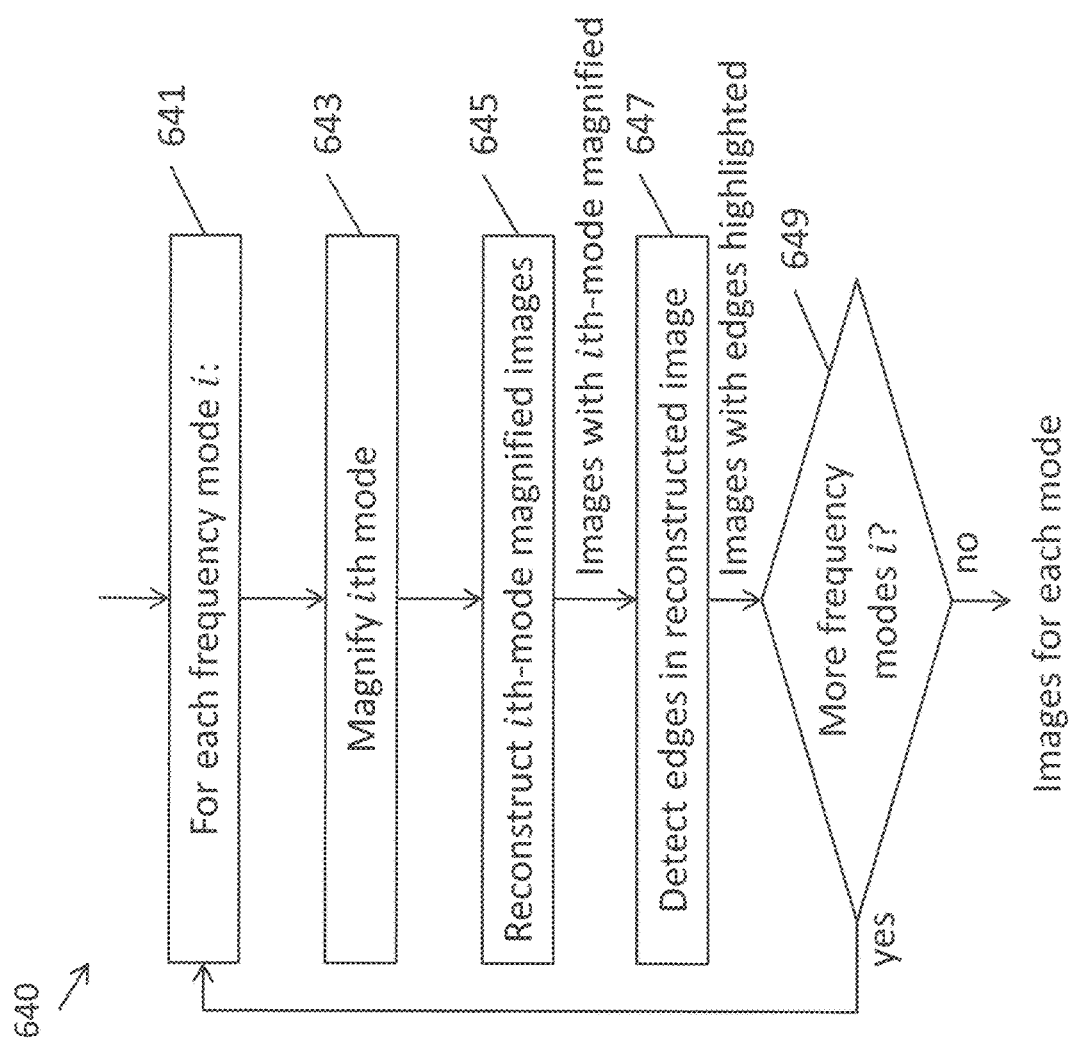
Figure 6C:
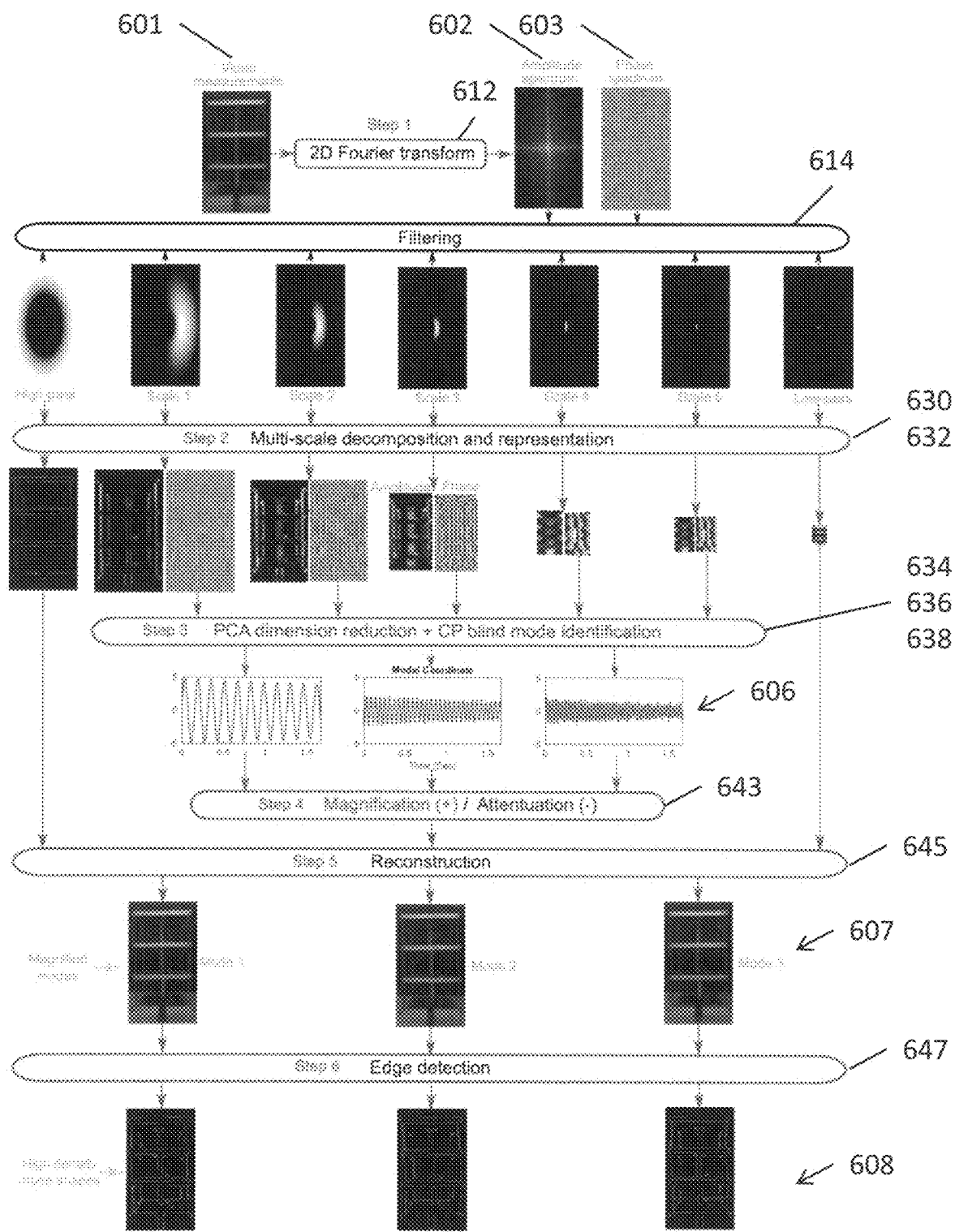

FIGS. 6A, 6B, and 6C are flowcharts illustrating a method 600 of computing according to one embodiment of the present invention. Embodiments of the present invention may be implemented using, for example, an image processing system or a video processing system such as a computer system (e.g., including a central processing unit or CPU coupled to memory), an image signal processor (ISP), a field programmable gate array (FPGA), a graphics processing unit (GPU), or other computing device or processor, or combinations thereof. In addition, the method may be spread or distributed across multiple computing devices or processors. For example, the computer may include a multi-core processor, the computer may include one or more graphical processing units or image signal processors, or the computation can be distributed across a cluster of computers (each of which may include one or more CPUs and zero or more GPUs). For the sake of convenience, the term "processor" will be used herein to refer to any type or system of one or more computing devices that is capable of performing the method.

For example, as shown in FIG. 22, some embodiments of the present invention may be implemented by a computer system that includes a processor 220 that is coupled to a video camera 224 for capturing video frames (e.g., images) of a structure. The processor 220 may also be coupled to memory 222 for storing instructions to be executed by the processor, as well as the images captured by the video camera 224 and working data, such as transformed video data, and output data. The processor 220 also be coupled to a display device 226 for displaying the reports or other outputs of the analysis of the video frames captured by the video camera 224.

Generally, in operations 612 and 614, spatial multi-scale decomposition and representation are performed by applying complex steerable pyramid filters on each frame $I(x+\delta(x,t))$ of the video (see Equation (1)) to obtain the filter response (sub-band representation) $R_\omega(x,t)$ on each spatial scale $\omega$ (see Equation (2)). In particular, in one embodiment, in operation 612 the processor computes two dimensional (2D) Fourier transforms of the frames 601 (e.g., image frames or frames of video) to obtain amplitude spectrum 602 and phase spectrum information 603 from the image frames 601. As noted above with reference to Equation (1), a complex steerable pyramid may be applied to the image frames in order to obtain multi-scale, localized, non-aliasing sub-bands for extracting the local amplitudes and local phases. In operation 614, the processor filters the Fourier transformed images to compute a filter response (sub-band representation) $R_\omega(x,t)$ on each spatial scale $\omega$ (see Equation (2)).

The following computations of the spatial scales w are independent of one another, and therefore each spatial scale may be computed in serially, or may be processed in parallel. For the sake of convenience, FIG. 6A depicts the processing of each spatial scale $\omega$ serially, but embodiments of the present invention are not limited thereto. In operation 620, the processor iterates over the spatial scales $\omega$.

In operation 630, from $R_\omega(x,t)$, the processor obtains the local phases $\psi(x,t)$ at each pixel of each frame, and in operation 632 the processor removes the temporal mean of $\psi(x,t)$ to obtain vibration motion $\delta'(x,t)$ (see Equation (3)).

In operation 634, on each scale $\omega$ of the multi-scale decomposition, the processor performs dimension reduction on the vibration motion $\delta'(x,t)$ using principal component analysis to obtain r active principal components $\eta$ with active non-zero singular values. In operation 636, the processor separates the principal components $\eta$ using, for example, blind source separation, on the active principal components $\eta$ to obtain the modal coordinates $q_i(x,t)$ (i=1, . . . , r) 606, and estimates the frequency and damping ratio from the modal coordinates in operation 638 (see Equation (12)).

In operation 640, the processor computes magnified images 608 for the r modes. Referring to FIGS. 6B and 6C, on each scale $\omega$ of the multi-scale decomposition, for each mode i, in operation 643 the processor magnifies the ith mode by multiplying the modal coordinates $q_i(t)$ by $\alpha$ (e.g., where $\alpha > 1$) and $q_k(t)$ ($k \in [1,r] \neq i$) by $\beta$ (e.g., where $\beta = -1$), applies the inverse transform from (3) to (2) to obtain the magnified motion $\widehat{N}(x,t)$, and multiplies the original sub-band representation $R_\omega(x,t)$ by $e^{j\widehat{\delta}'}$ to obtain magnified sub-band representation $\hat{R}_\omega(x,t)$ (see Equation (18)).

In operation 645, the processor reconstructs the ith-mode-magnified image $\hat{I}(x+\delta'(x,t))$ by collapsing $\hat{R}_\omega(x,t)$ to generate reconstructed images with magnified modes 607.

In operation 647, the processor performs edge detection on the ith-mode-magnified image $\hat{I}$ to obtain high-resolution ith mode shapes 608 of the structure.

In operation 649, the processor determines if there are additional modes i to process in this way. If so, then the processor returns to operation 641 to select the next mode i. In some embodiments, the various modes may be processed in parallel rather than in series. The processor may then output the generated images for each mode.

Returning to FIG. 6A, in operation 650 (in an embodiment where the spatial scales $\omega$ are processed serially), the processor determines if there are any additional spatial scales to consider. If so, then the processor returns to operation 620 to select the next spatial scale. If not, then the processor outputs the amplified mode shape images computed for each of the spatial scales for each of the modes.

Differences from Related Art

While aspects of embodiments of the present invention build upon phase-based motion magnification techniques, it is considerably different from the existing work. Related motion magnification techniques generally require users to first specify the frequency band of the motion that the user is interested in and magnify the content within the specified frequency band. Specifically, after obtaining the local phase $R_\omega(x,t)$ as per Equation (1) to Equation (2), the original phase based technique temporally filters $R_\omega(x,t)$ into a user-specified frequency band of interest to magnify the filtered component. However, the frequency band containing the motion of interest is seldom known in advance, requiring trial-and-error on the part of the user and manual tuning of the parameters in the software application.

Some related work applies the phase-based motion magnification techniques for modal analysis. In this work, displacements were explicitly computed from the obtained local phases of a few predefined cropped regions of the images of the structure, which were called "virtual accelerometers." Then, a traditional peak-picking method was performed on the computed displacements to obtain the frequencies. According to the estimated frequencies, the frequency band of interest was specified and the whole process of the original phase-based motion magnification technique was then implemented. However, this related work does not address the weakly-excited mode identification issue because the peak-picking process used the user's judgement of the mode, which becomes very challenging when noise is present. In addition, when closely-spaced modes are present, they will overlap in the specified frequency band, in which case that method will not be able to separate and magnify each individual mode. Also, because of the user-defined cropped regions and the peak-picking process, such procedures are not automated.

In contrast, aspects of embodiments of the present invention apply unsupervised learning techniques such as blind source separation to manipulate only the local phase itself and, as a result, embodiments of the present invention are able to blindly separate the individual modal components (potentially even closely-spaced and highly-damped modes) for modal identification and magnification with little-to-no user supervision, thus avoiding the need for a user to search and specify the frequency bands of interest (or vibrational modes of interest) and addressing the issue of identifying and magnifying close modes. In addition, the aspects of embodiments of the present invention do not require the explicit computation of the displacements of the structure; rather, aspects of embodiments of the present invention can extract all modal parameters throughout the procedure without the need of calibration or surface preparation (e.g., high-contrast markers or random speckle pattern) as compared with traditional vision based methods.

Experimental Validation

Figure 7B:
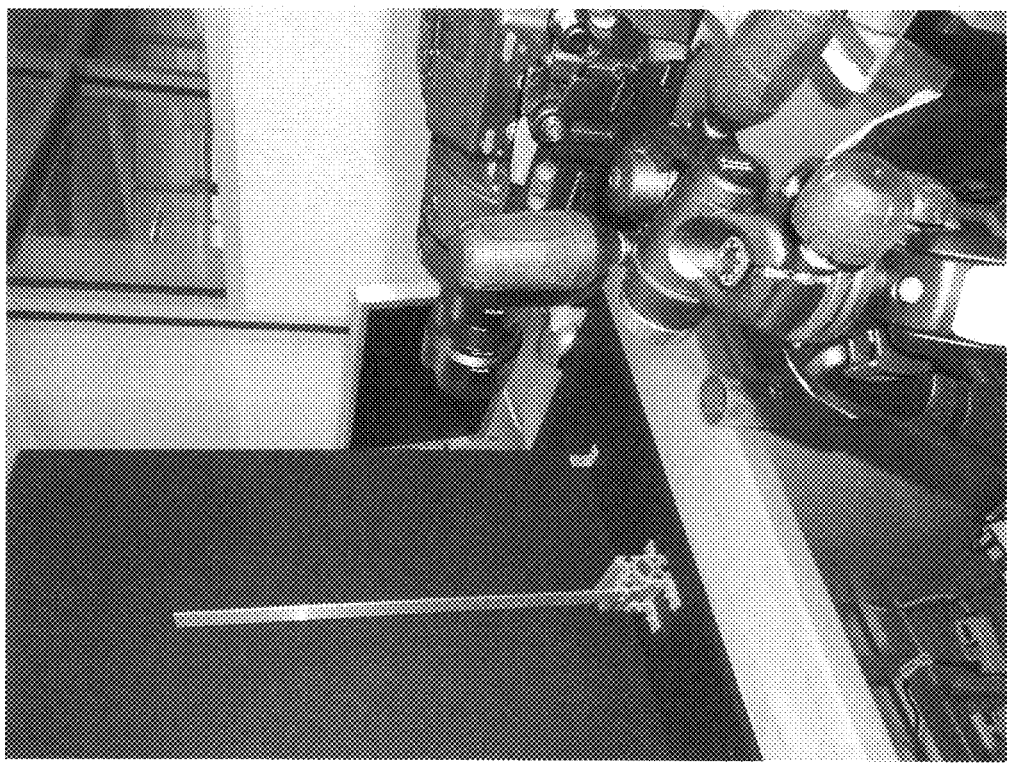
FIG. 7B is a photograph of an experimental setup of a bench-scale model of an aluminum cantilever beam (continuous-type) structure, which was used to validate one embodiment of the present invention.
Figure 7A:
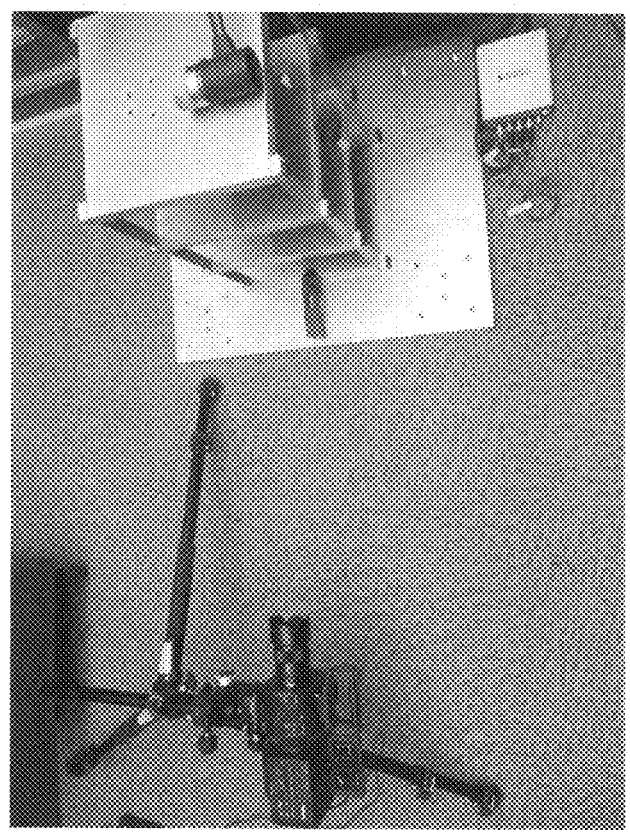
FIG. 7A is a photograph of an experimental setup of a bench-scale model of a three-story (discrete-type) building structure was used to validate one embodiment of the present invention.

FIG. 7A is a photograph of an experimental setup of a bench-scale model of a three-story (discrete-type) building structure was used to validate one embodiment of the present invention. The structure was constructed of aluminum columns and lumped mass plates on each floor, with its base fixed to a heavy solid aluminum plate on the ground. An impact hammer was used to excite the structure horizontally on the top floor. A stationary camera (a Sony® NXCAM® with a pixel resolution of 1920×1080) mounted with a Zeiss® lens with a fixed focal length of 24 mm was used to perform video measurements of the structure at a frame rate of 240 frames per second. The illumination environment is the ordinary indoor lighting condition of the laboratory without any external illumination enhancement (e.g., additional lighting).

In some embodiments of the present invention, the maximum frequency of vibrations detectable by the system are limited (due to the sampling theorem) to half of the frame rate. For instance, in the above example in which video is captured at a frame rate of 240 frames per second, the maximum detectable vibration frequency in the structure is 240 fps/2=120 fps or 120 Hz. In other embodiments of the present invention, the video may be captured at a higher frame rate (e.g., 480 frames per second), thereby allowing the detection of higher frequency vibrations, in accordance with the Nyquist sampling theorem. In still other embodiments of the present invention, a regular commercial-grade digital video camera (e.g., capturing frames at 24 frames per second, 30 frames per second, or 60 frames per second) may be sufficient, in accordance with the Nyquist sampling theorem (for example, in circumstances where the vibrational modes of interest in the structure may be less than 12 Hz, 15 Hz, or 30 Hz).

In other embodiments of the present invention, the full-field mode shapes can be extracted, even when the video is temporally aliased because there are vibrational modes above the Nyquist frequency (e.g., vibrational modes frequencies greater than half the frame rate of the video camera).

For comparison, three uniaxial accelerometers attached on each floor of the structure were used to measure the accelerations, from which the modal parameters were also extracted and compared with those estimated from the video measurements using a method according to one embodiment of the present invention.

Implementation Procedures and Results

For more efficient computation, the images captured by the stationary camera at the pixel resolution of 1920×1080 were downsampled to a pixel resolution of 384×216 and a set of video measurements of 400 frames in total (less than two seconds in duration at 240 frames per second). FIGS. 8A-1, 8A-2, 8A-3, and 8A-4 depict a few selected frames from the video captured of an experimental setup shown in FIG. 7A according to one embodiment of the present invention. FIGS. 8B-1, 8B-2, 8B-3, and 8B-4 depict a few selected frames from the video captured of an experimental setup shown in FIG. 7B according to one embodiment of the present invention.

Figure 9:
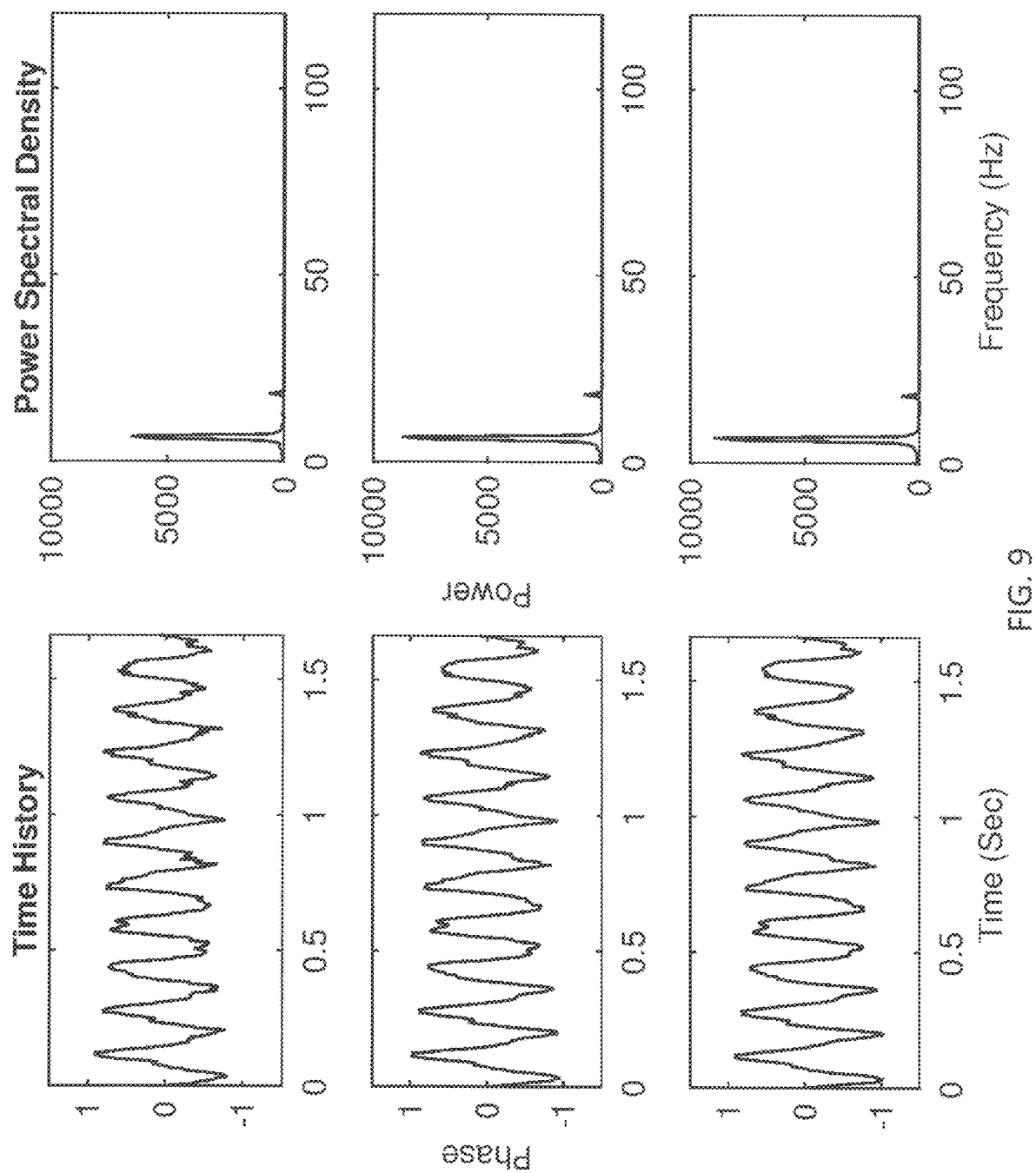
FIG. 9 shows the time history and power spectra of the phases of some three pixels on the first sub-band (Scale 1), which correspond to the structural vibration responses from the video measurements of the building structure shown in FIG. 7A.

Methods according to embodiments of the present invention are automated. First, each frame is decomposed and represented by a five-scale complex pyramid (sub-bands) with the high-pass and low-pass components. The time histories of the local phases of each pixel of each frame, on each scale, were then extracted. FIG. 9 shows the time history and power spectra of the phases of some three pixels on the first sub-band (Scale 1), which correspond to the structural vibration responses from the video measurements of the building structure shown in FIG. 7A.

Figure 10:
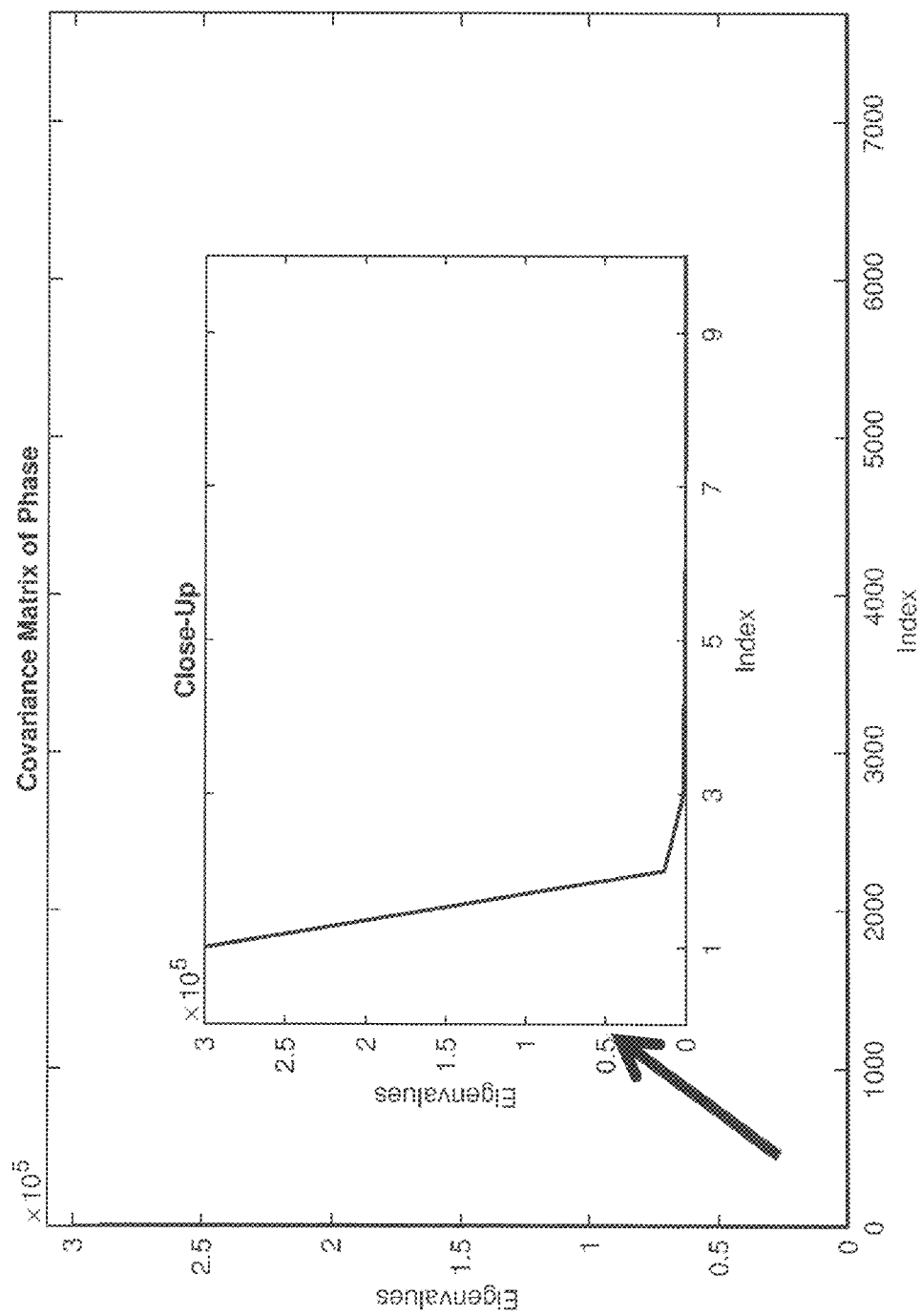
FIG. 10 is a graph of the eigenvalue distribution of the phase covariance matrix $\delta' \delta'^{*}$.
Figure 11:
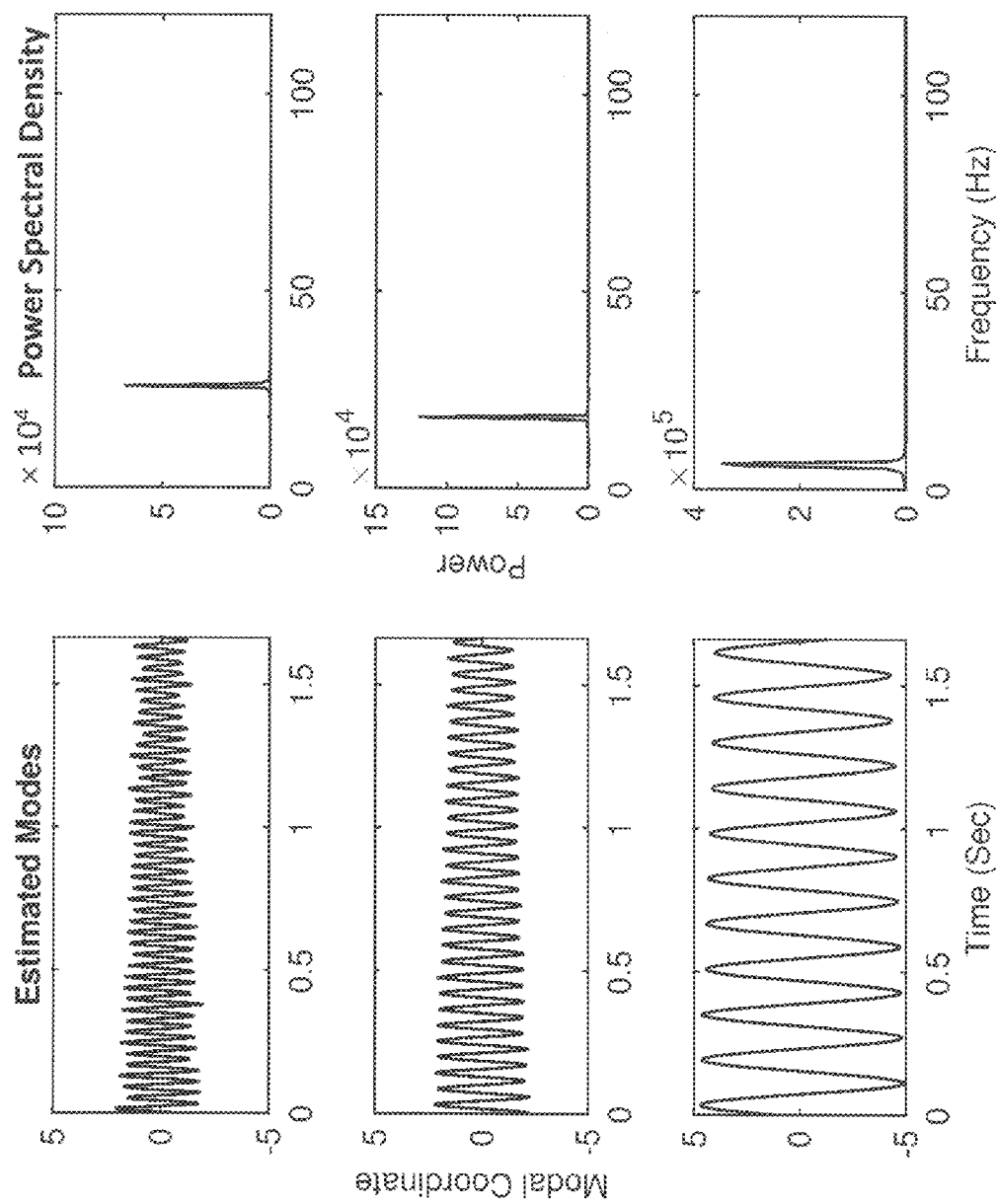
FIG. 11 illustrates estimated modal coordinates by the complexity pursuit (CP) algorithm applied on the active principal components of the spatio-temporal pixel phases of the video of the building structure.
Figures 1, 12A:
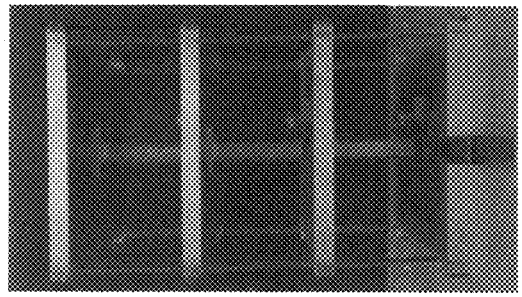
Figures 1, 12B:
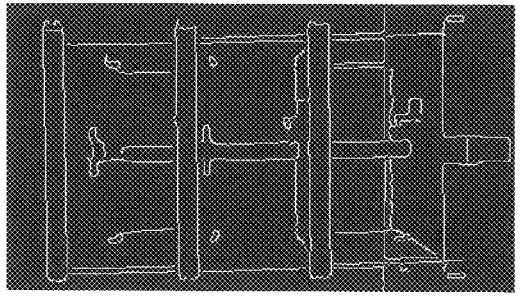
Figures 2, 12A:
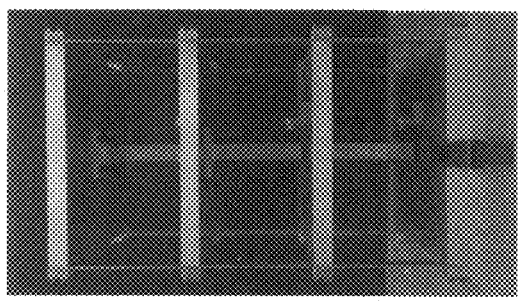
Figures 2, 12B:
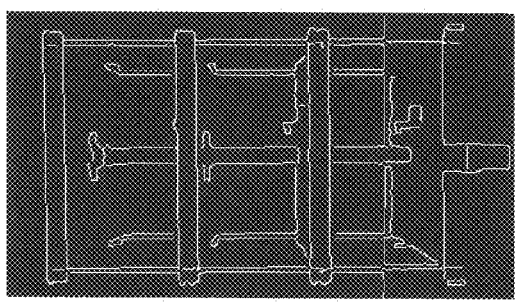
Figures 3, 12A:
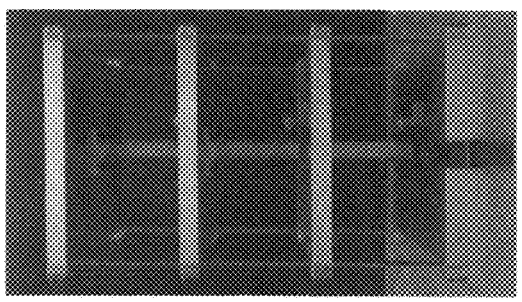
Figures 3, 12B:
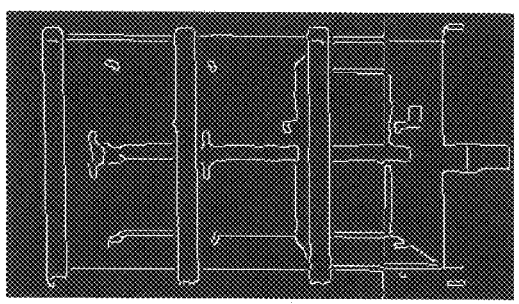
Figures 4, 12A:
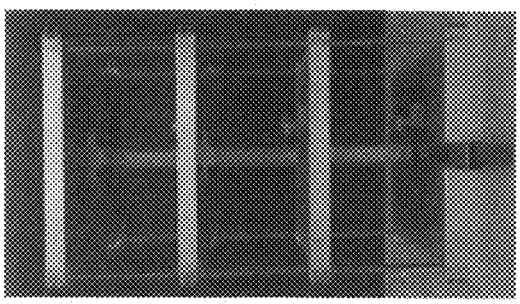
Figures 4, 12B:
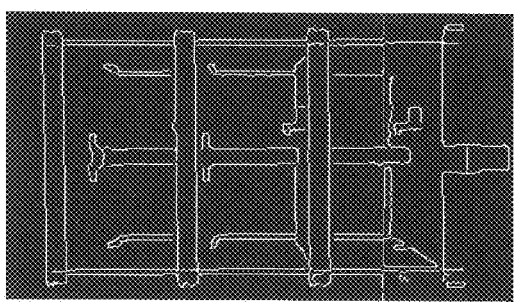
Figures 1, 13A:
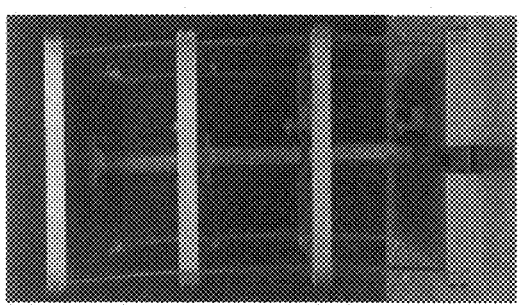
Figures 2, 13A:
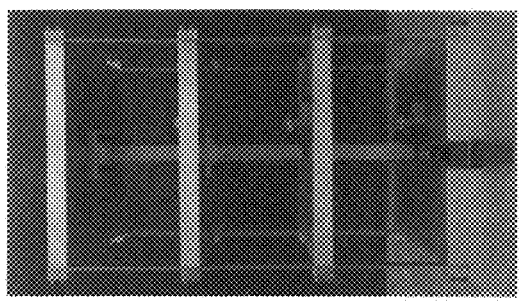
Figures 3, 13A:
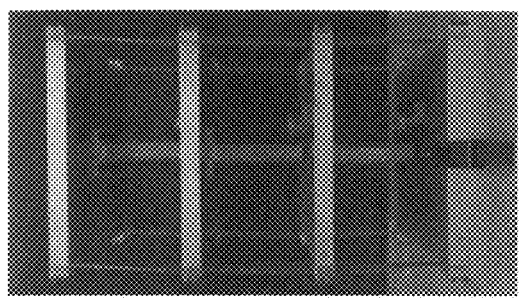
Figures 4, 13A:
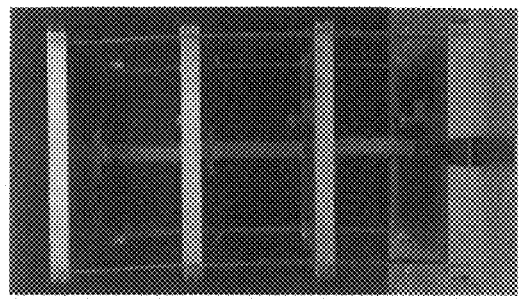
Figures 1, 13B:
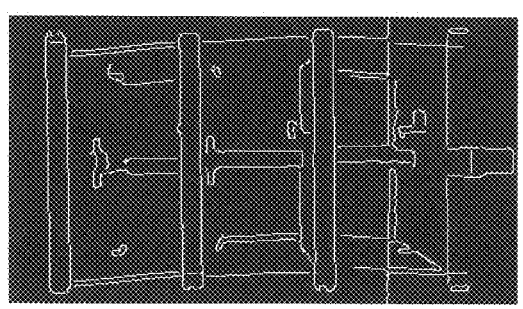
Figures 2, 13B:
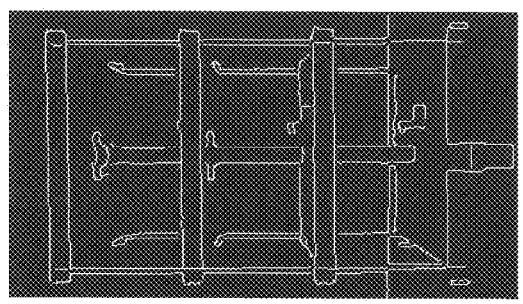
Figures 3, 13B:
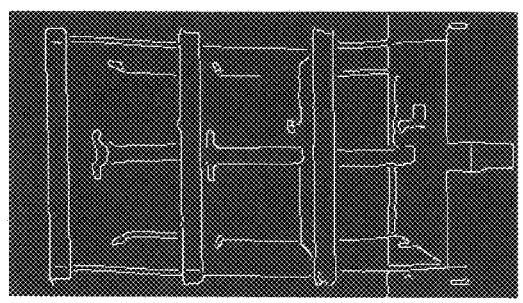
Figures 4, 13B:
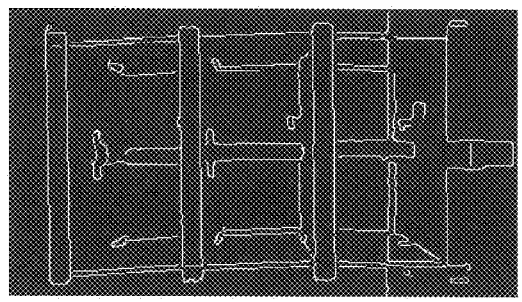
Figures 4, 14A:
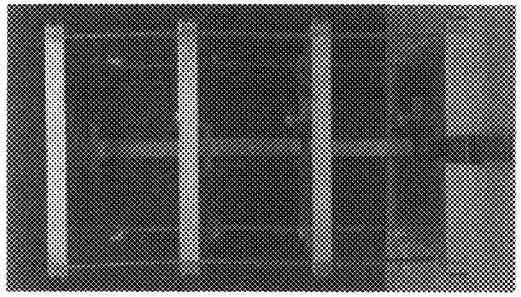
Figures 4, 14B:
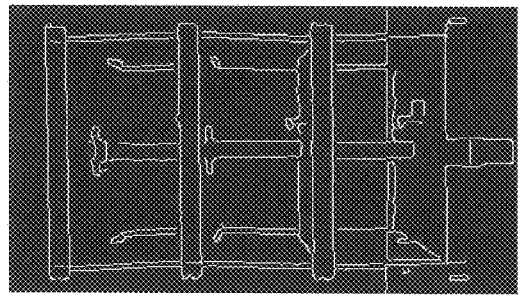
Figures 3, 14A:
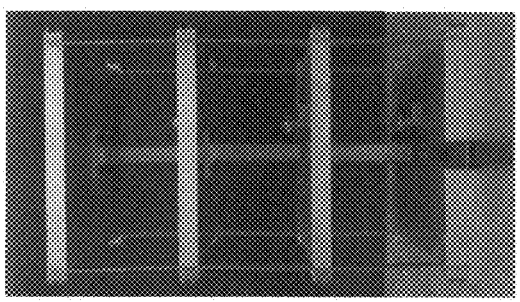
Figures 3, 14B:
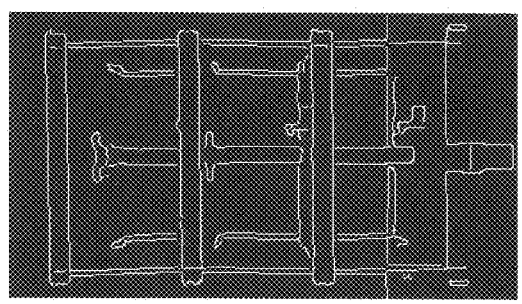
Figures 2, 14A:
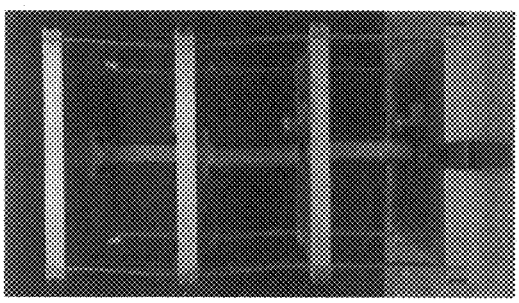
Figures 2, 14B:
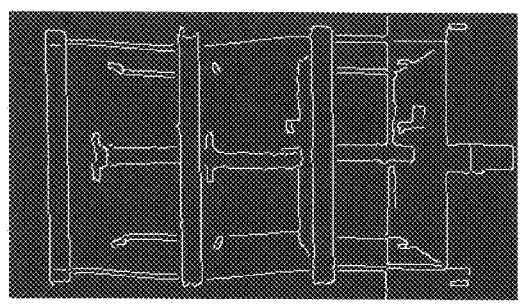
Figures 1, 14A:
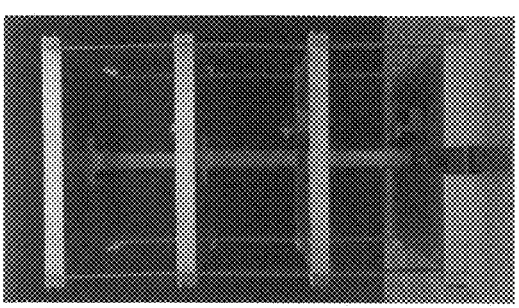
Figures 1, 14B:
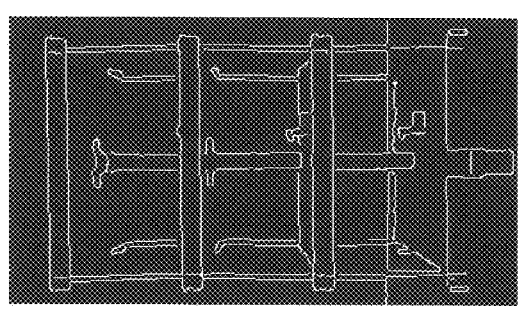

On each scale, PCA is then performed on the obtained phase matrix $\delta'$. During the PCA dimension reduction process, the eigenvalue decomposition on the covariance matrix of $\delta'$ was conducted to determine the active principal components $\eta$. For illustrations, FIG. 10 is a graph of the eigenvalue distribution of the phase covariance matrix $\delta' \delta'^*$. It is seen that the eigenvalues decay radically: although the pixel dimension is on order of thousands, only the first three principal components are active, i.e., $r \approx 3$. For automated selection of the active principal components, a thresholding eigenvalue was set below 1% of the largest eigenvalue (meaning it is relatively very small) and more than 50% of the previous eigenvalue (meaning the decay has been stabilized). FIG. 11 illustrates estimated modal coordinates by the complexity pursuit (CP) algorithm applied on the active principal components of the spatio-temporal pixel phases of the video of the building structure. The three principal components $\eta(t)$ were then decomposed by the blind source separation (BSS) technique complexity pursuit (CP), yielding the three monotone modal coordinates (t) (i=1, 2, 3), as shown in FIG. 11. Hilbert transform based SDOF technique and the logarithm decrement technique were applied on the estimated modal coordinates to obtain the frequency and damping ratio, respectively. These results are shown in Table 2, below:

TABLE 2

The modal parameters of the 3-story structure estimated from the video measurements compared to those estimated from accelerometers

| | Frequency (Hz) | | Damping ratio (%) | |
|---|---|---|---|---|
| Mode | Accelerometer | Video | Accelerometer | Video |
| 1 | 6.27 | 6.31 | 0.28 | 0.27 |
| 2 | 17.88 | 17.92 | 0.30 | 0.30 |
| 3 | 25.82 | 25.92 | 0.25 | 0.25 |

The measured accelerations were directly decoupled by CP into individual modal coordinates (see FIGS. 16A and 16B), from which the frequency and damping ratio were also estimated by the Hilbert transform based SDOF method and the logarithm decrement technique. Table 2 shows that the results of the two output-only methods are in excellent agreement. As demonstrated, the video measurement based methods according to embodiments of the present invention are able to estimate the very high-resolution operational mode shapes, while the accelerometer based method can only provide mode shapes at limited discrete points (three in this experiment).

FIGS. 12A-1, 12A-2, 12A-3, and 12A-4 illustrate a few temporal frames from the motion magnified video (Mode 1, $\alpha$=8) of the building structure of FIG. 7A, and FIGS. 12B-1, 12B-2, 12B-3, and 12B-4 depict the corresponding mode shapes found by performing edge detection on the frames shown in FIGS. 12A-1, 12A-2, 12A-3, and 12A-4. FIGS. 13A-1, 13A-2, 13A-3, and 13A-4 illustrate a few temporal frames from the motion magnified video (Mode 2, $\alpha$=40) of the building structure of FIG. 7A, and FIGS. 13B-1, 13B-2, 13B-3, and 13B-4 depict the corresponding mode shapes found by performing edge detection on the frames shown in FIGS. 13A-1, 13A-2, 13A-3, and 13A-4.

The phase-based motion magnification technique can significantly magnify the motion of the vibration without increasing the noise intensity level (because the magnification technique has the effect of shifting the phase of the noise instead), which is especially useful for identification of the weakly-excited mode with very subtle vibration motion that is easily contaminated by noise. In this experiment it is seen in FIG. 9 that the 3rd mode is barely present in the video measurement of the structural responses. To demonstrate the advantage of using motion magnification, the result of the 3rd mode without magnification (setting $\alpha$=1) is shown in FIGS. FIGS. 17A-1, 17A-2, 17A-3, 17A-4, 17B-1, 17B-2, 17B-3, and 17B-4, indicating that the vibration motion is extremely weak (barely visible) and vulnerable to noise contamination, which increase the uncertainty of the estimation accuracy of this weak mode. However, by applying the motion magnification technique, the vibration motion of the 3rd mode, which would otherwise be very weak, is easily seen and can be reliably extracted from the magnified video of this mode, as shown in FIGS. FIGS. 14A-1, 14A-2, 14A-3, 14A-4, 14B-1, 14B-2, 14B-3, and 14B-4, which illustrates, in a first row, a few temporal frames from the motion magnified video (Mode 3, $\alpha$=70) of the building structure and, in a second row, their corresponding mode shapes found by performing edge detection.

Figures 15A, 15B, 15C:
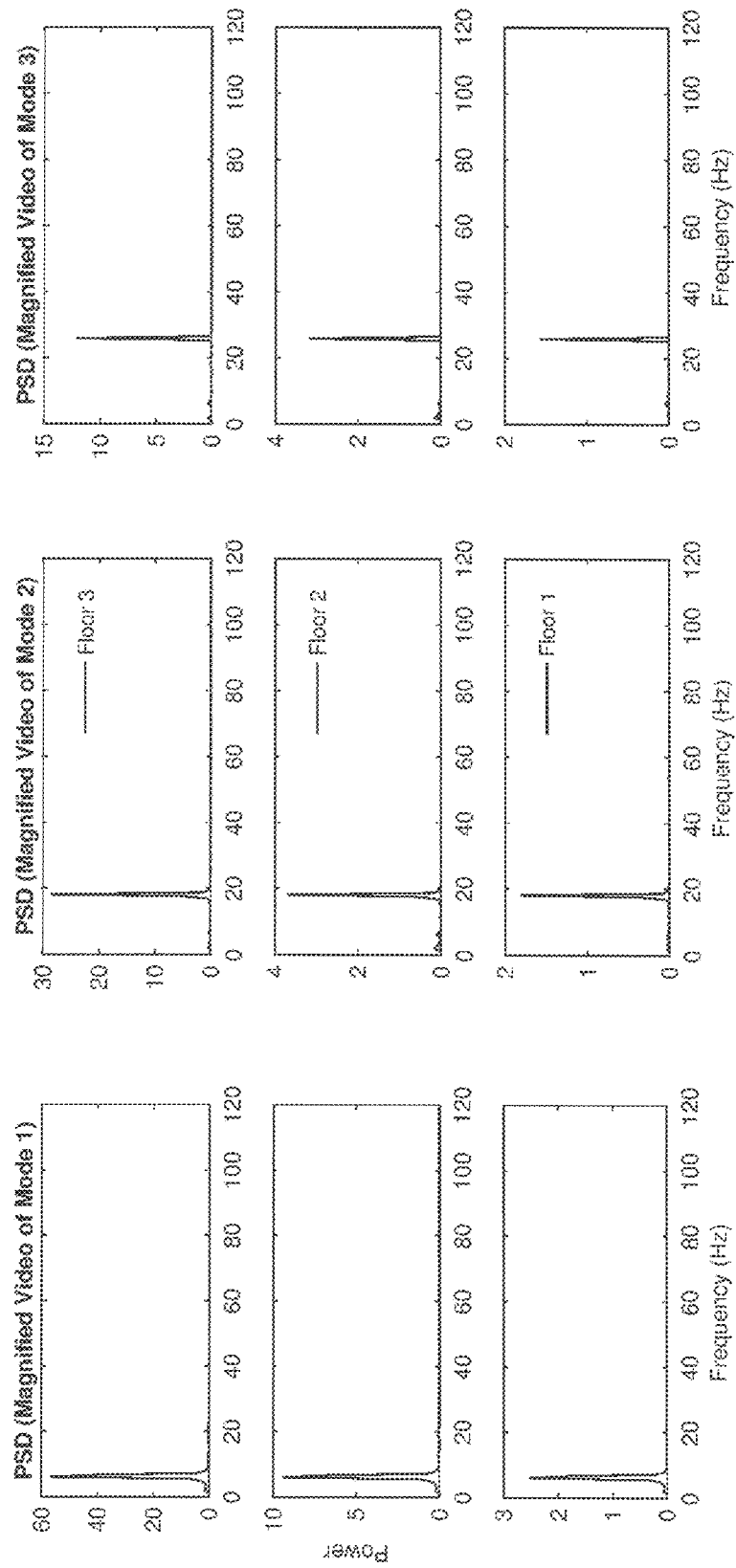
FIGS. 15A, 15B, and 15C illustrate the power spectral density (PSD) of the estimated motion field of some regions (distributed on different floors) of the building structure shown in FIG. 7A of the motion-magnified videos of different modes.

FIGS. 15A, 15B, and 15C illustrate the power spectral density (PSD) of the estimated motion field of some regions (distributed on different floors) of the building structure shown in FIG. 7A of the motion-magnified videos of different modes.

Figure 16A:
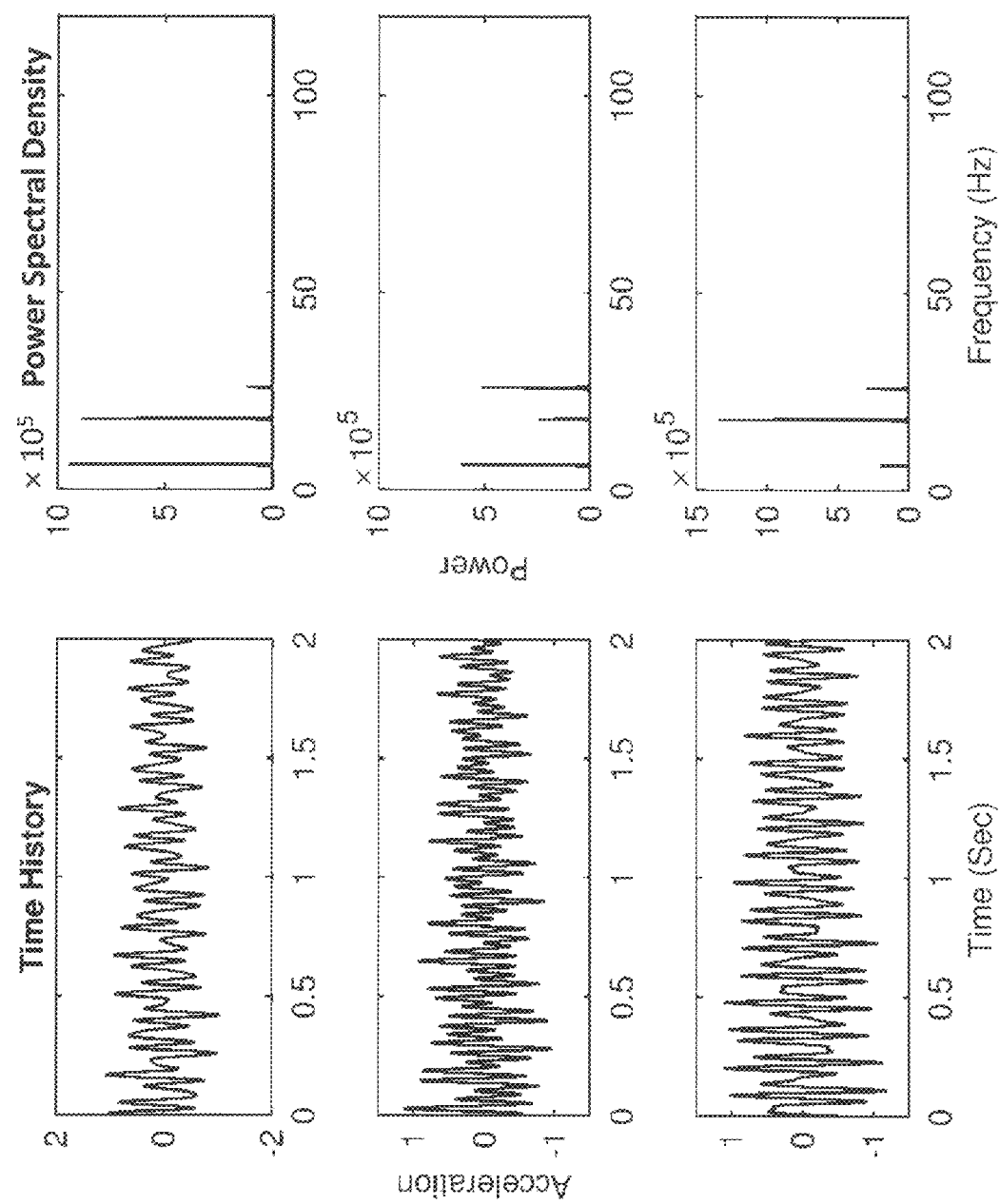
FIG. 16A illustrates the measured accelerations on the three floors of the building structure shown in FIG. 7A and their power spectral density (PSD).

FIG. 16A illustrates the measured accelerations on the three floors of the building structure and their power spectral density (PSD).

Figure 16B:
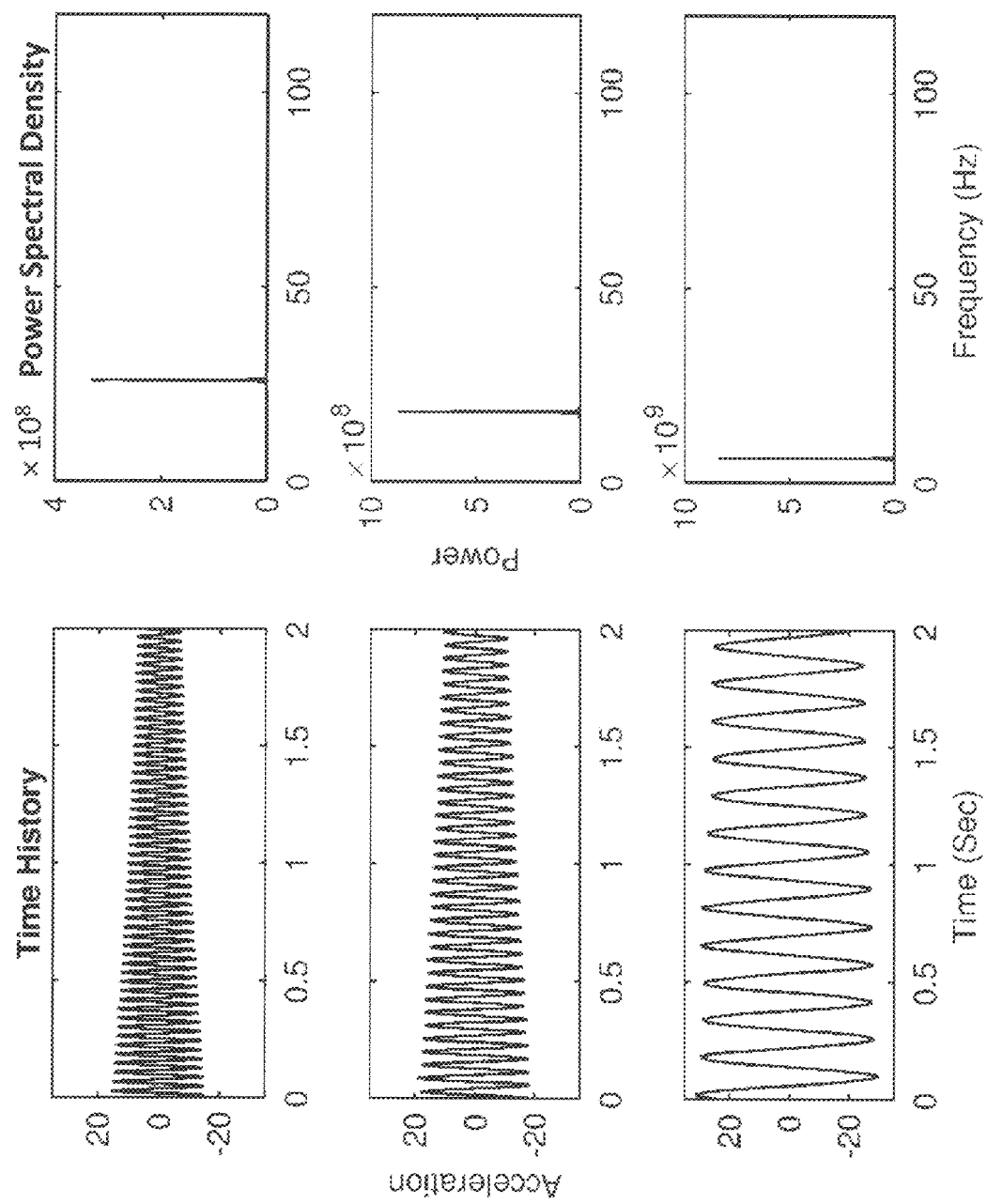
FIG. 16B illustrates the estimated modal coordinates by complexity pursuit (CP) algorithm according to one embodiment of the present invention from the accelerations in FIG. 16A and their PSD.
Figures 4, 17A:
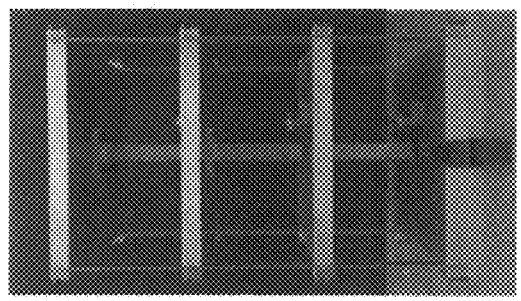
Figures 4, 17B:
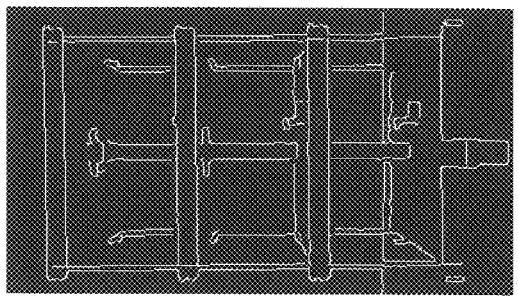
Figures 3, 17A:
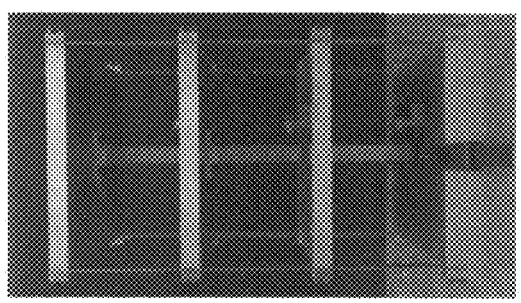
Figures 3, 17B:
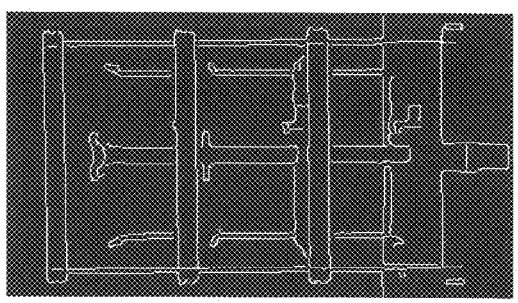
Figures 2, 17A:
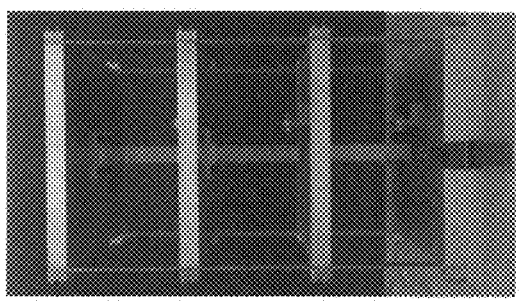
Figures 2, 17B:
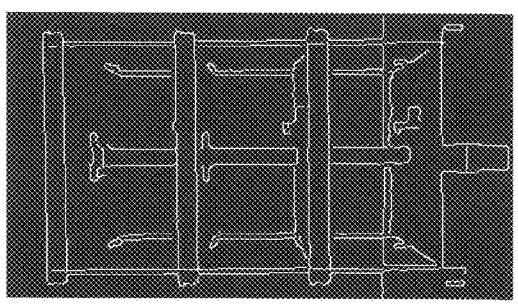
Figures 1, 17A:
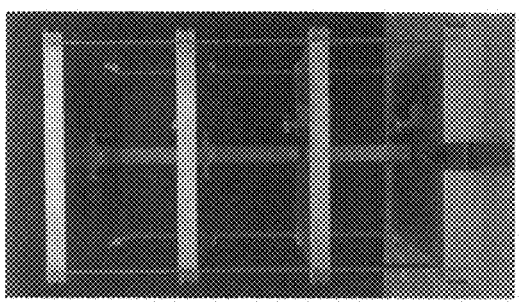
Figures 1, 17B:
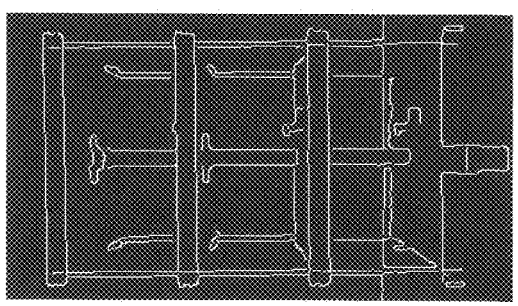

FIG. 16B illustrates the estimated modal coordinates by complexity pursuit (CP) algorithm according to one embodiment of the present invention from the accelerations in FIG. 16A and their PSD.

FIGS. 17A-1, 17A-2, 17A-3, and 17A-4 illustrate a few temporal frames from the non-magnified Video (Mode 3, $\alpha$=1) of the building structure of FIG. 7A and, FIGS. 17B-1, 17B-2, 17B-3, and 17B-4 depict the corresponding mode shapes found by performing edge detection on the frames shown in FIGS. 17A-1, 17A-2, 17A-3, and 17A-4.

Related motion magnification techniques and related work applying this technique to modal analysis requires users to first specify the frequency band of the interested modal motion and magnify the component within the specified frequency band. In contrast, embodiments of the present invention use unsupervised learning algorithms such as BSS to blindly identify modal components of interest for magnification, thus removing the need of optical flow computation of the displacements of some cropped region that was required in related work. In addition, in some embodiments of the present invention, the separated modal component (potentially close to other modes) is directly magnified with a single frequency instead of a frequency band that could incorporate multiple, closely-spaced modes. Unlike related work, embodiments of the present invention can be implemented autonomously within the modified phase-based motion magnification framework with little-to-no user input and/or supervision.

Generally, optical measurement methods such as DIC, point-tracking, and the optical flow methods are based on processing image intensity, which is known to be sensitive to illumination environment. On the other hand, aspects of embodiments of the present invention are based on phase manipulation, which is less sensitive to the light, surface, and perspective conditions.

In related phase-based motion magnification techniques, the magnified motion $(1+\alpha)\delta_{(i)}'$ of the ith mode is bounded by the spatial support of the transfer function (complex Gabor wavelet) on each scale. As the motion $\delta_{(i)}'$ of the weak mode (the 3rd mode in this experiment) is much smaller than others, its $\alpha_1$ can be set larger. In the above experimental example, the values were set at: $\alpha_1$=8, $\alpha_2$=40, and $\alpha_3$=70. It was found through experimentation that the value of a can be set in a wide range (to several hundreds) with satisfactory results. In some embodiments of the present invention, the steerability of the complex steerable pyramid method can be utilized to extend the analysis for modal analysis of multi-dimensional vibration of structures with more complex geometry.

Figures 4, 8A:
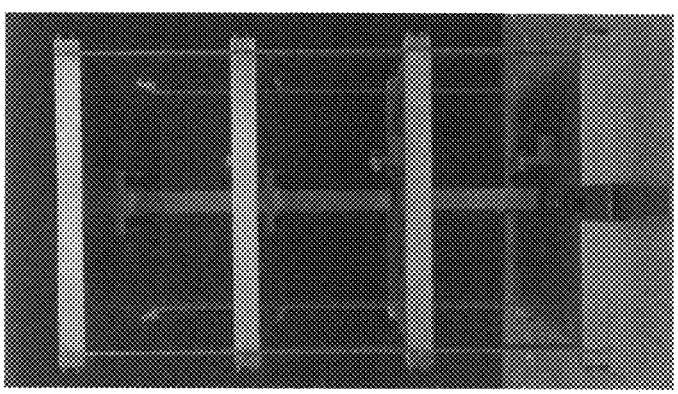
Figures 3, 8A:
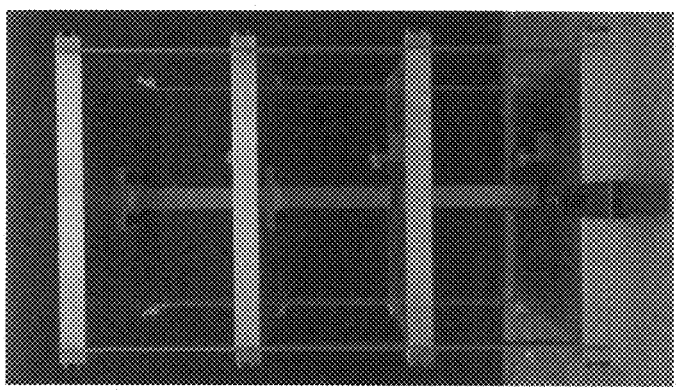
Figures 2, 8A:
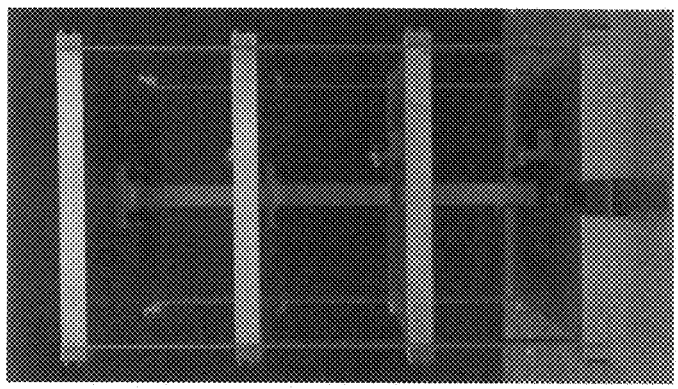
Figures 1, 8A:
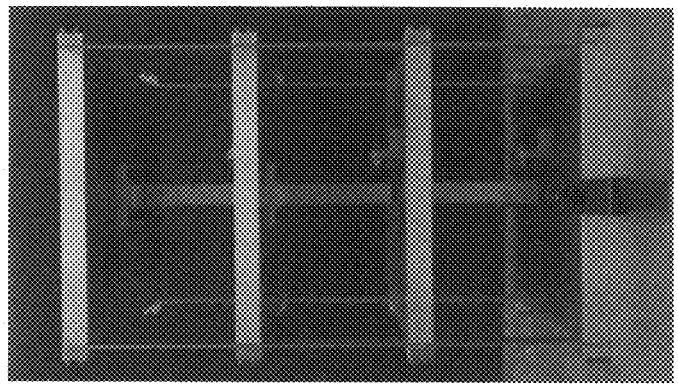
Figures 4, 8B:
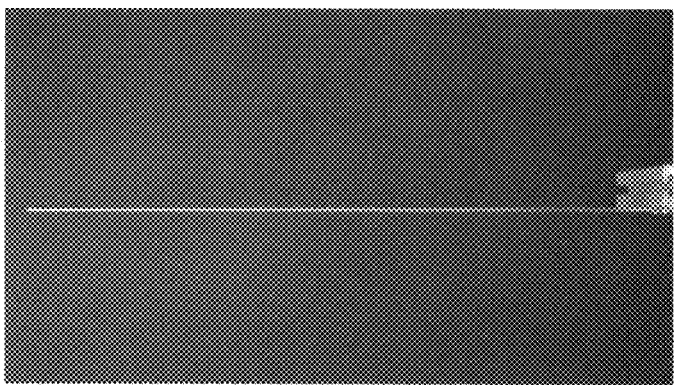
Figures 3, 8B:
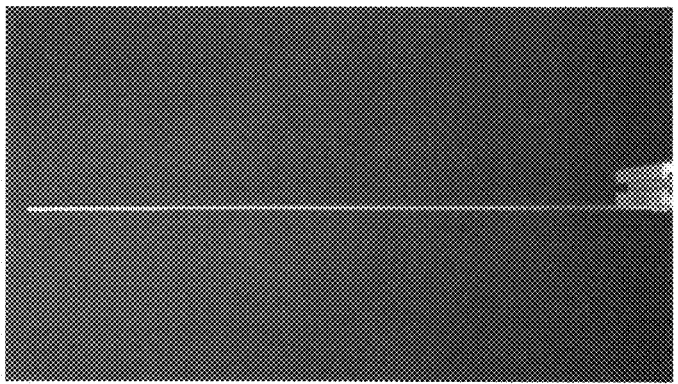
Figures 2, 8B:
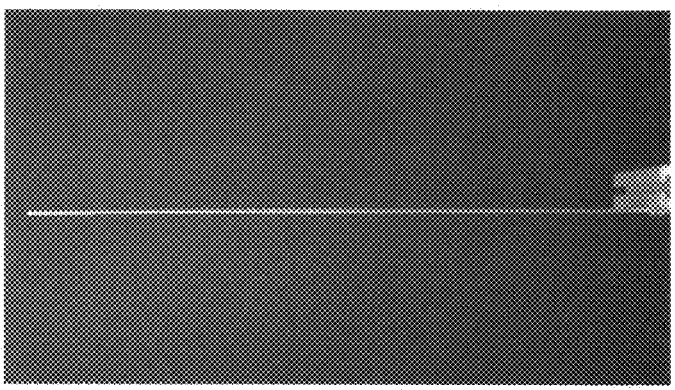
Figures 1, 8B:
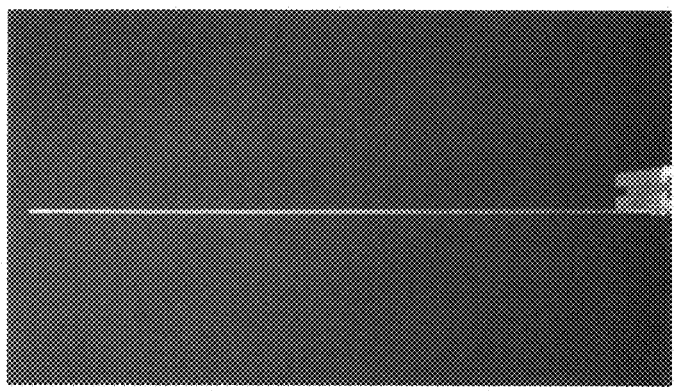

In addition to the above structure having three floors, a bench-scale model of an aluminum cantilever beam (continuous-type) structure was also used to validate the method according to embodiments of the present invention. An impact hammer was used to excite the beam horizontally close to the fixed end. The same camera and lens were used to perform video measurements of the beam at a frame rate of 480 frames per second (FIG. 7B). In this arrangement, the pixels were downsampled to 384×216 and a set of video measurements with less than two seconds in duration including 600 frames in total was used. FIG. 8(b) shows selected frames from the video measurements.

Figure 18:
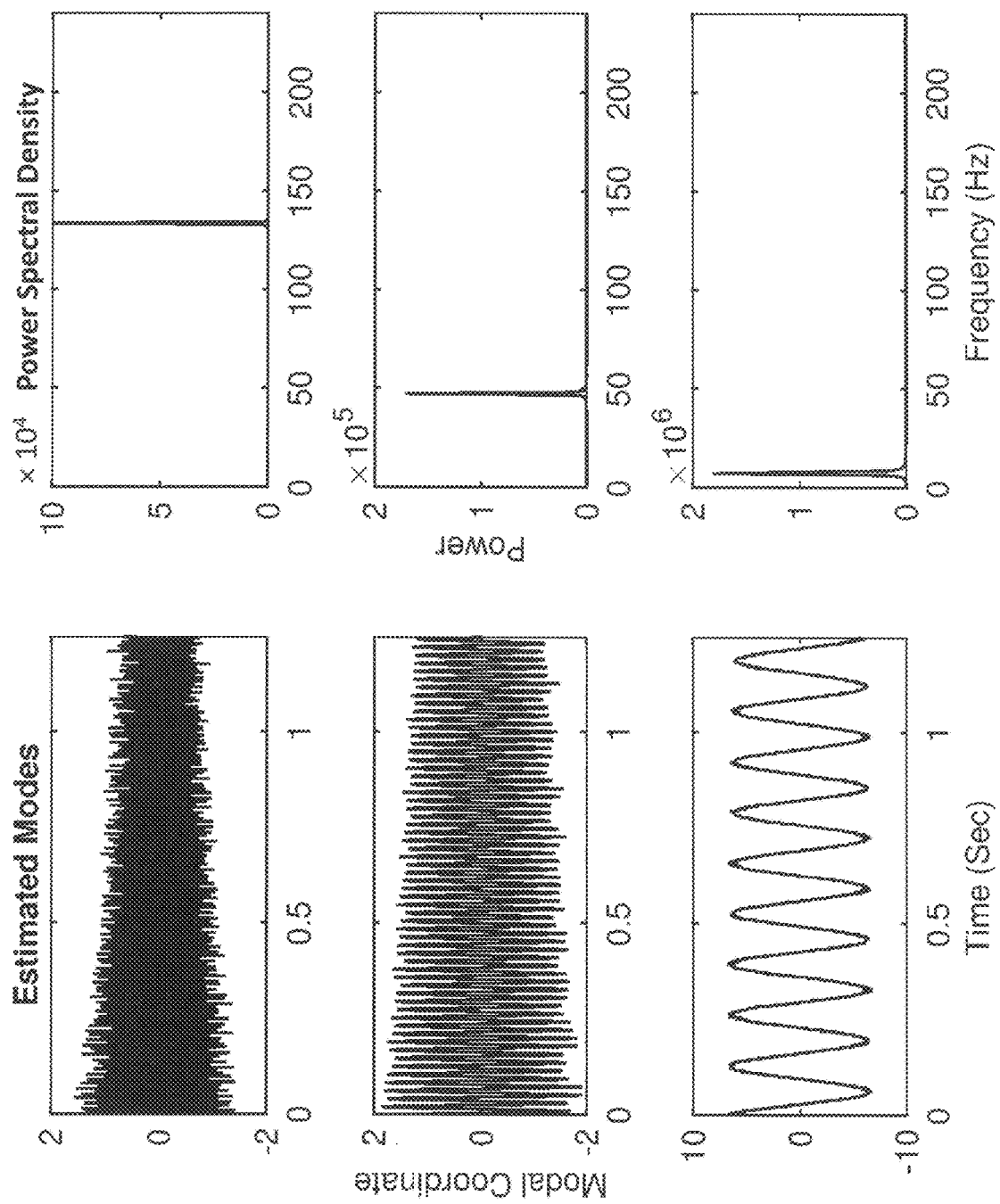
FIG. 18 illustrates the estimated modal coordinates by the complexity pursuit (CP) algorithm applied on the active principal components of the spatio-temporal pixel phases of the video of the beam structure shown in FIG. 7B.
Figures 4, 19A:
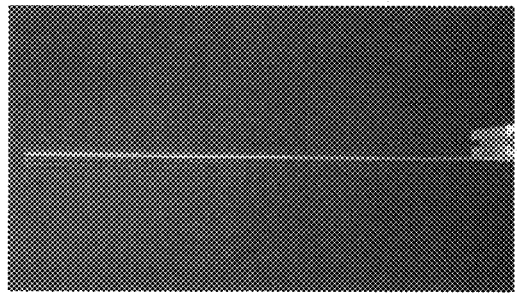
Figures 4, 19B:
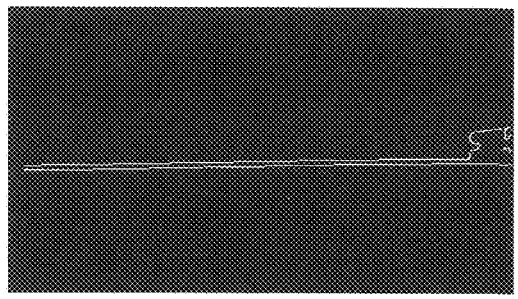
Figures 2, 19A:
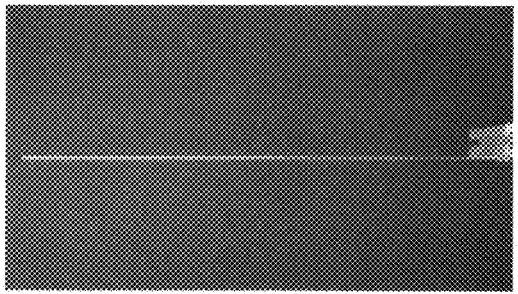
Figures 2, 19B:
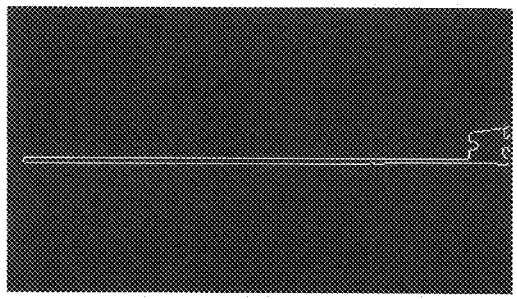
Figures 1, 19A:
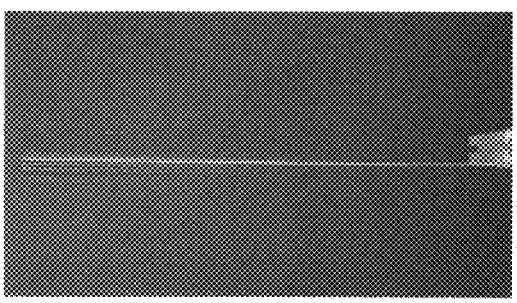
Figures 1, 19B:
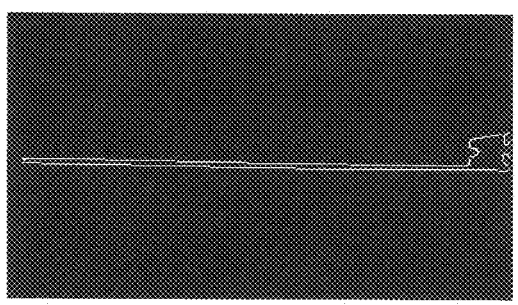

FIG. 18 illustrates the estimated modal coordinates by the complexity pursuit (CP) algorithm applied on the active principal components of the spatio-temporal pixel phases of the video of the beam structure shown in FIG. 7B. Three dominant modes were identified with modal frequencies of 7.5 Hz, 48.2 Hz, and 133.6 Hz, as shown in FIG. 18, which are consistent with those identified from accelerometers attached to the beam. The magnified videos of each of the three modes are demonstrated in FIGS. 19, 20, and 21, showing the high-resolution mode shapes. These mode shapes are consistent with those predicted by the dynamic theory of beam-type structures.

FIGS. 19A-1, 19A-2, 19A-3, and 19A-4 illustrate a few temporal frames from the motion magnified video of the beam structure of FIG. 7B (Mode 1, $\alpha$=8), and FIGS. 19B-1, 19B-2, 19B-3, and 19B-4 depict the corresponding mode shapes found by performing edge detection on the frames shown in FIGS. 19A-1, 19A-2, 19A-3, and 19A-4.

FIGS. 20A-1, 20A-2, 20A-3, and 20A-4 illustrate a few temporal frames from the motion magnified video of the beam structure of FIG. 7B (Mode 2, $\alpha$=25) and FIGS. 20B-1, 20B-2, 20B-3, and 20B-4 depict the corresponding mode shapes found by performing edge detection on the frames shown in FIGS. 20A-1, 20A-2, 20A-3, and 20A-4.

FIGS. 21A-1, 21A-2, 21A-3, and 21A-4 illustrate a few temporal frames from the motion magnified video of the beam structure of FIG. 7B (Mode 3, $\alpha$=45) and FIGS. 21B-1, 21B-2, 21B-3, and 21B-4 depict the corresponding mode shapes found by performing edge detection on the frames shown in FIGS. 21A-1, 21A-2, 21A-3, and 21A-4.

As such, embodiments of the present invention relate to a full-field, output-only (video measurement) modal analysis algorithm in the modified phase-based video motion magnification framework. It combines a multi-scale pyramid decomposition and representation method and an unsupervised learning blind source separation (BBS) technique to model and manipulate the spatiotemporal pixel phases that encode the local structural vibration in the video measurements, thus capable of blindly and accurately extracting the modal frequencies, damping ratio, and high-resolution mode shapes of the structure.

Compared to existing vision-based methods, embodiments of the present invention require no structural surface preparation (e.g., the use of markers or speckle patterns) and perform the data capture and analysis in a relatively efficient and autonomous manner. Compared to the closely-related phase-based motion magnification based method, embodiments of the present invention require minimal user input and supervision, does not require explicit optical flow computation, and can detect and separate closely-spaced and highly-damped modes.

In addition, embodiments of the present invention are robust against noise of phase-based motion magnification is motivated and interpreted in identification and visualization of the weakly-excited mode with subtle vibration motion in the structural responses, which is a common and challenging issue in operational modal identification. Laboratory experiments are demonstrated to validate the developed method with comparisons to the accelerometer measurement based method.

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof.

For example, while embodiments of the present invention are described in the context of evaluating physical structures, and while the experiments were performed on physical structures, embodiments of the present invention are not limited thereto and can be applied to detecting and analyzing vibrational dynamics of other physical processes. These may include the dynamics of biological cells growing in a controlled environment, fluid dynamics, and micro-expressions in video images of human faces.

As noted above, while embodiments of the present invention are described above with respect to using digital video cameras to capture images, embodiments of the present invention are not limited thereto and can be used with other data acquisition systems such as data collected by sensors including stereo cameras, depth cameras, light field imagers, electron microscopes, thermal imagers, hyper/multispectral imagers, event-based silicon retinas, and medical imaging technologies (e.g., ultrasonography or ultrasound, magnetic resonance imaging, and positron emission tomography). Embodiments of the present invention may be applicable to any imaging technology that collects sequences of frames, whether collected in two dimensions (2D) or three dimensions (3D).

Embodiments of the present invention are described above as extracting motion from the video image using a phase-based approach, but embodiments of the present invention are not limited thereto. For example, in other embodiments of the present invention, the motion is extracted by using other techniques such as Lagrangian (motion of particles is tracked in time), Eulerian (properties of a voxel evolve in time), as well as optical flow-based approaches such as those based on Lucas Kanade 1981 and Horn and Schunk 1981. Embodiments of the present invention can be applied to any technique that provides motion estimates from video images.

Dimensionality reduction serves the purpose of reducing the amount of data that computations must be performed on. In addition it helps make the form of the data more suitable for the dynamics extraction step that follows. Embodiments of the present invention are described above with respect to using principal component analysis for dimensionality reduction of the motion estimates. However, a wide variety of dimensionality reduction techniques may be used instead. Examples include Kernel PCA, Graph-based kernel principal component analysis, manifold learning, Isomap, locally linear embedding, Laplacian eigenmaps, autoencoders, and maximum variance unfolding, linear discriminant analysis, canonical correlation analysis. Note that these are all more advanced dimension reduction techniques that require extensive computation and user expertise for implementation, although any dimensionality reduction technique should work in principle. In some cases it may be advantageous select the dimensionality reduction technique based on the nature of the dynamics extraction technique that follows, such as nonlinear dynamic features.

Embodiments of the present invention are described above with respect to extracting the dynamics from the motion estimates using the Complexity Pursuit solution to the problem of blind source separation. However, a variety of blind source separation techniques can address this problem. Any form of decomposition algorithm could be used on all the measurements to extract the dynamics. These include techniques such as principal component analysis (PCA), independent component analysis (ICA), autoencoders, and second order blind identification (SOBI). As would be understood by one of skill in the art, the previously mentioned dimensionality reduction technique can be matched with the dynamics extraction technique depending on the nature of the problem to be analyzed.

For example, the use of PCA-CP algorithm in blindly (unsupervised), automatically (no user expertise needed), and very efficiently (within a couple of minutes) extracting the high-resolution dynamics of a wide range of structures is related to the physical connection between the linear PCA-CP machine learning model and the general dynamic model of any linear structures. However, embodiments of the present invention are not limited thereto and can be used with other alternatives, as appropriate to the circumstances being analyzed.

What is claimed is:

1. A method for automatically extracting vibrational modes of a structure, the method comprising:
   receiving, by a processor, a plurality of video frames, each of the video frames comprising a plurality of pixels;
   decomposing, by the processor, each of the video frames on a plurality of spatial scales in accordance with complex steerable pyramid filters to obtain a filter response for each of the spatial scales;
   computing, by the processor, a plurality of local phases of the pixels of each frame;
   removing, by the processor, a temporal mean from each frame to obtain a plurality of factored vibration motion functions;
   performing, by the processor, principal component analysis on the factored vibration motion functions to obtain principal components;

blind source separating, by the processor, the principal components to compute a plurality of modal coordinates;

magnifying an ith modal coordinate of the modal coordinates by:
   scaling the ith modal coordinate by a positive coefficient to compute a scaled ith modal component;
   scaling each non-ith modal coordinate other than the ith modal coordinate by a negative coefficient to compute one or more non-ith scaled modal coordinates; and
   applying an inverse transform on the scaled ith modal coordinate and the one or more non-ith scaled modal coordinates to compute an ith-mode magnified vibration motion function;

computing, by the processor, frequency and damping ratios in accordance with the modal coordinates; and outputting, by the processor, the computed frequency and damping ratios.

2. The method of claim 1, further comprising outputting the ith-mode magnified vibration motion function as a factored vibration motion function.

3. The method of claim 1, further comprising reconstructing a plurality of ith mode magnified images based on the ith mode magnified vibration motion function.

4. The method of claim 3, further comprising outputting the ith magnified images as a video.

5. The method of claim 3, further comprising:
performing edge detection on the ith mode magnified image to generate magnified ith mode shapes; and
outputting the magnified ith mode shapes.

6. The method of claim 5, further comprising outputting the magnified ith mode shapes as a video.

7. The method of claim 1, wherein the video frames are received from a video camera, the video frames being captured by the video camera at a rate of at least 240 frames per second.

8. The method of claim 1, wherein the video frames are received from a video camera, the video frames being captured by the video camera at a rate of at least 24 frames per second.

9. A system for automatically extracting vibrational modes of a structure comprising:
a processor; and
memory coupled to the processor, the memory having instructions stored there on that, when executed by the processor, cause the processor to:
   receive a plurality of video frames, each of the video frames comprising a plurality of pixels;
   decompose each of the video frames on a plurality of spatial scales in accordance with complex steerable pyramid filters to obtain a filter response for each of the spatial scales;
   compute a plurality of local phases of the pixels of each frame;
   remove a temporal mean from each frame to obtain a plurality of factored vibration motion functions;
   perform principal component analysis on the factored vibration motion functions to obtain principal components;
   blind source separate the principal components to compute a plurality of modal coordinates;
   magnify an ith modal coordinate of the modal coordinates by:
     scaling the ith modal coordinate by a positive coefficient to compute a scaled ith modal component;
     scaling each non-ith modal coordinate other than the ith modal coordinate by a negative coefficient to compute one or more non-ith scaled modal coordinates; and
     applying an inverse transform on the scaled ith modal coordinate and the one or more non-ith scaled modal coordinates to compute an ith-mode magnified vibration motion function;
   compute frequency and damping ratios in accordance with the modal coordinates; and
   output the computed frequency and damping ratios.

10. The system of claim 9, wherein the memory further stores instructions that, when executed by the processor, cause the processor to output the ith-mode magnified vibration motion function as a factored vibration motion function.

11. The system of claim 9, wherein the memory further stores instructions that, when executed by the processor, cause the processor to reconstruct a plurality of ith mode magnified images based on the ith mode magnified vibration motion function.

12. The system of claim 11, wherein the memory further stores instructions that, when executed by the processor, cause the processor to output the ith magnified images as a video.

13. The system of claim 11, wherein the memory further stores instructions that, when executed by the processor, cause the processor to:
perform edge detection on the ith mode magnified image to generate magnified ith mode shapes; and
output the magnified ith mode shapes.

14. The system of claim 13, wherein the memory further stores instructions that, when executed by the processor, cause the processor to output the magnified ith mode shapes as a video.

15. The system of claim 9, further comprising a video camera, the video camera being configured to capture the video frames at a rate of at least 240 frames per second.

16. The system of claim 9, further comprising a video camera, the video camera being configured to capture the video frames at a rate of at least 24 frames per second.

17. A system for automatically extracting vibrational modes of a structure, the system comprising:
means for receiving a plurality of video frames, each of the video frames comprising a plurality of pixels;
means for decomposing each of the video frames on a plurality of spatial scales in accordance with complex steerable pyramid filters to obtain a filter response for each of the spatial scales;
means for computing a plurality of local phases of the pixels of each frame;
means for removing a temporal mean from each frame to obtain a plurality of factored vibration motion functions;
means for performing principal component analysis on the factored vibration motion functions to obtain principal components;
means for blind source separating the principal components to compute a plurality of modal coordinates;
means for magnifying an ith modal coordinate of the modal coordinates by:
   scaling the ith modal coordinate by a positive coefficient to compute a scaled ith modal component;
   scaling each non-ith modal coordinate other than the ith modal coordinate by a negative coefficient to compute one or more non-ith scaled modal coordinates; and applying an inverse transform on the scaled ith modal coordinate and the one or more non-ith scaled modal coordinates to compute an ith-mode magnified vibration motion function;

means for computing frequency and damping ratios in accordance with the modal coordinates; and means for outputting the computed frequency and damping ratios.

* * * * *